United States Patent
Fujimura et al.

(10) Patent No.: US 9,980,643 B2
(45) Date of Patent: May 29, 2018

(54) OPHTHALMOLOGIC APPARATUS

(71) Applicant: KABUSHIKI KAISHA TOPCON, Itabashi-ku (JP)

(72) Inventors: Takashi Fujimura, Fujimino (JP); Taisaku Kogawa, Mitaka (JP); Ryuichi Morishima, Itabashi-ku (JP); Hiroaki Okada, Saitama (JP); Takefumi Hayashi, Wako (JP)

(73) Assignee: KABUSHIKI KAISHA TOPCON, Itabashi-ku (JP)

( * ) Notice: Subject to any disclaimer, the term of this patent is extended or adjusted under 35 U.S.C. 154(b) by 0 days. days.

(21) Appl. No.: 15/233,616

(22) Filed: Aug. 10, 2016

(65) Prior Publication Data

US 2016/0345822 A1   Dec. 1, 2016

Related U.S. Application Data

(62) Division of application No. 14/396,220, filed as application No. PCT/JP2013/060993 on Apr. 11, 2013, now Pat. No. 9,526,416.

(30) Foreign Application Priority Data

May 1, 2012   (JP) .................................. 2012-104976
Nov. 30, 2012   (JP) ................................ 2012-261893

(51) Int. Cl.
*A61B 3/14*   (2006.01)
*A61B 3/15*   (2006.01)
*A61B 3/00*   (2006.01)

(52) U.S. Cl.
CPC .............. *A61B 3/15* (2013.01); *A61B 3/0025* (2013.01); *A61B 3/0058* (2013.01);
(Continued)

(58) Field of Classification Search
CPC .. A61B 3/15; A61B 3/145; A61B 3/14; A61B 3/0025; A61B 3/0058; A61B 3/0083; A61B 3/152; A61B 3/154
(Continued)

(56) References Cited

U.S. PATENT DOCUMENTS 5,596,377 A   1/1997   Yano
5,696,573 A   12/1997   Miwa
(Continued)

FOREIGN PATENT DOCUMENTS

EP   2 138 093 A1   12/2009
GB   2 293 659 A   4/1996
(Continued)

OTHER PUBLICATIONS

Extended European Search Report dated Jan. 11, 2016 in Patent Application No. 13784763.8.
(Continued)

*Primary Examiner* — William R Alexander
(74) *Attorney, Agent, or Firm* — Oblon, McClelland, Maier & Neustadt, L.L.P.

(57) ABSTRACT

An ophthalmologic apparatus which is capable of preferably executing position matching between an eye and optical system is provided. An ophthalmologic apparatus of an embodiment includes an examination optical system, supporting part, driver, two or more imaging parts, analyzer and controller. The examination optical system is used for an examination of the eye. The supporting part supports a face of a subject. The driver moves the examination optical system and the supporting part relatively and three-dimensionally. The two or more imaging parts substantially simultaneously photograph an anterior eye part of the eye from different directions. The analyzer obtains a three-dimensional position of the eye by analyzing two or more photo-
(Continued)

graph images acquired by the two or more imaging parts substantially simultaneously. The controller controls the driver based on the three-dimensional position to relatively move the examination optical system and the supporting part.

35 Claims, 16 Drawing Sheets

(52) U.S. Cl.
CPC .............. *A61B 3/0083* (2013.01); *A61B 3/14* (2013.01); *A61B 3/145* (2013.01); *A61B 3/152* (2013.01); *A61B 3/154* (2013.01)

(58) Field of Classification Search
USPC ................................. 351/208, 200, 205, 206
See application file for complete search history.

(56) References Cited

U.S. PATENT DOCUMENTS

| | | | |
|---|---|---|---|
| 5,784,148 A | 7/1998 | Heacock | |
| 5,909,269 A | 6/1999 | Isogai et al. | |
| 6,661,571 B1* | 12/2003 | Shioda | A61B 1/04 359/368 |
| 7,478,909 B2 | 1/2009 | Masaki | |
| 7,922,327 B2 | 4/2011 | Su | |
| 8,363,783 B2* | 1/2013 | Gertner | A61B 3/113 351/206 |
| 2003/0160942 A1 | 8/2003 | Xie | |
| 2004/0114107 A1 | 6/2004 | Mimura | |
| 2005/0105049 A1 | 5/2005 | Maeda | |
| 2006/0103724 A1 | 5/2006 | Jongsma | |
| 2007/0030446 A1 | 2/2007 | Su | |
| 2007/0051362 A1 | 3/2007 | Sullivan | |
| 2008/0204656 A1 | 8/2008 | Fujita | |
| 2008/0252850 A1 | 10/2008 | Plagwitz | |
| 2010/0053556 A1 | 3/2010 | Muller | |
| 2010/0128960 A1 | 5/2010 | Yumikake | |
| 2010/0165293 A1 | 7/2010 | Tanassi et al. | |
| 2010/0172567 A1 | 7/2010 | Prokoski | |
| 2011/0080561 A1 | 4/2011 | Hayashi | |
| 2011/0109877 A1 | 5/2011 | Pujol Ramo | |
| 2012/0019780 A1 | 1/2012 | Nozato | |

FOREIGN PATENT DOCUMENTS

| | | |
|---|---|---|
| JP | 58-97340 A | 6/1983 |
| JP | 2-134130 A | 5/1990 |
| JP | 5-56927 | 3/1993 |
| JP | 8-103414 A | 4/1996 |
| JP | 8-117188 A | 5/1996 |
| JP | 8-299267 A | 11/1996 |
| JP | H10-216089 A | 8/1998 |
| JP | 2004-174155 A | 6/2004 |
| JP | 2004-298460 A | 10/2004 |
| JP | 2005-287782 | 10/2005 |
| JP | 2006-280612 A | 10/2006 |
| JP | 4136690 | 8/2008 |
| JP | 2009-112664 | 5/2009 |
| JP | 2010-12109 | 1/2010 |
| JP | 2011-200281 A | 10/2011 |
| WO | WO 01/24688 A1 | 4/2001 |

OTHER PUBLICATIONS

International Search Report dated May 14, 2013, in PCT/JP13/060993 filed Apr. 11, 2013.
Office Action dated Apr. 11, 2017 in Japanese Patent Application No. 2016-156590.
Office Action dated Apr. 11, 2017 in Japanese Patent Application No. 2016-156591.
Office Action dated Jan. 16, 2018, in corresponding Japanese Patent Application No. 2017-077463 (with English Translation).
Office Action dated Apr. 17, 2018, in corresponding Japanese Patent Application No. 2017-077463 (with Machine English Translation), 9 pages.

* cited by examiner

OPHTHALMOLOGIC APPARATUS

The present application is a divisional of U.S. application Ser. No. 14/396,220 filed on Oct. 22, 2014, which is a National Stage of PCT/JP2013/060993, filed Apr. 11, 2013, and claims priority to Japanese Patent Application No. 2012-104976, filed May 1, 2012, and Japanese Patent Application No. 2012-261893, filed Nov. 30, 2012, the entire contents of each of which are incorporated herein by reference.

TECHNICAL FIELD

The present invention relates to an ophthalmologic apparatus that optically examines an eye.

BACKGROUND TECHNOLOGY

Types of ophthalmologic apparatuses include ophthalmologic imaging apparatuses for obtaining images of an eye and ophthalmologic measuring apparatuses for measuring characteristics of an eye.

Examples of ophthalmologic imaging apparatuses include an optical coherence tomography (OCT) apparatus that obtains cross sectional images using OCT, a retinal camera that photographs a fundus, a Scanning Laser Ophthalmoscope (SLO) that obtains images of a fundus by laser scanning with a confocal optical system, a slit lamp that obtains images by photographing an optical section of a cornea using slit light, etc.

Moreover, examples of ophthalmologic measuring apparatuses include an eye refractivity examination apparatus (refractometer, keratometer) that measures refractive properties of an eye, a tonometer, a specular microscope that obtains properties of a cornea (cornea thickness, cellular distribution, etc.), a wave-front analyzer that obtains aberration information of an eye using a Shack-Hartmann sensor, etc.

Regarding ophthalmic examinations using these apparatuses, in terms of precision and accuracy of examinations, position matching between the optical system of the apparatus and an eye is very important. This position matching includes alignment and tracking. Alignment includes the action of aligning the light axis of the optical system of the apparatus with respect to the axis of an eye (xy alignment), as well as the action of adjusting the distance between the eye and the optical system of the apparatus (z alignment). Tracking is an action of detecting the movement of an eye and changing the position of the optical system of the apparatus in accordance with the eye.

PRIOR ART DOCUMENT

Patent Document

[Patent Document 1] Japanese Laid-open Patent Publication No. 2009-112664
[Patent Document 2] Japanese Patent No. 4136690

Problem to be Solved by the Invention

According to conventional position matching techniques, position matching in the xy-direction (i.e. direction perpendicular to an optical axis) and position matching in the z-direction (i.e. direction along an optical axis) are carried out with different methods. That is, it is necessary to detect positional relationship between an eye and an optical system of an apparatus in order to execute position matching; however, positional relationship in the xy-direction and positional relationship in the z-direction are obtained with different methods. Thereby, an error occurs between both position matching methods, resulting in deterioration in accuracy of images and measurements acquired and deterioration in repeatability of examination, etc. Further, complication of configuration of apparatuses, such as necessity of preparing two different optical systems and calculation functions corresponding to two different methods of position matching, is also a problem.

Further, an ophthalmologic apparatus is provided with a chin rest and forehead rest for supporting a face of a subject and fixing position of an eye. Conventionally, position adjustment of the chin rest and forehead rest is carried out by a user's operation. Adjustment of height position of an optical system of an apparatus is also carried out by a user. These operations deteriorate efficiency of imaging and measurement, which may be a burden to a subject and examiner.

Further, it has been difficult for a conventional ophthalmologic apparatus to determine whether positional relationship between an eye and optical system is getting closer to or getting away from an appropriate state while moving the optical system, the chin rest, etc. In fact, only one method has been applied for conventional ophthalmologic apparatuses in which the optical system etc. is moved to a desired position once and then the above determination is carried out by referring an infrared observation image acquired in this state etc.

An objective of the present invention is to provide an ophthalmologic apparatus that is capable of preferably executing position matching between an eye and optical system of the apparatus.

Means for Solving the Problem

A first aspect is an ophthalmologic apparatus comprising: an examination optical system configured for carrying out an examination of an eye; a supporting part configured to support a face of a subject; a driver configured to move the examination optical system and the supporting part relatively and three-dimensionally; two or more imaging parts configured to substantially simultaneously photograph an anterior eye part of the eye from different directions; an analyzer configured to obtain a three-dimensional position of the eye by analyzing two or more photograph images acquired by the two or more imaging parts substantially simultaneously; and a controller configured to control the driver based on the three-dimensional position to relatively move the examination optical system and the supporting part.

A second aspect is the ophthalmologic apparatus of the first aspect, wherein the driver comprises a first driver configured to move the examination optical system three-dimensionally, and the controller controls the first driver based on the three-dimensional position so as to align an optical axis of the examination optical system with an axis of the eye and adjust a distance between the eye and the examination optical system to a preset working distance.

A third aspect is the ophthalmologic apparatus of the second aspect, wherein the analyzer comprises: a characteristic position specifying part configured to analyze the two or more photograph images to specify characteristic positions in the photograph images that correspond to a predetermined characteristic part of the anterior eye part; and a three-dimensional position calculating part configured to calculate, as the three-dimensional position of the eye, a three-dimensional position of the characteristic part based on positions of the two or more imaging parts and the characteristic positions in the two or more photograph images.

A fourth aspect is the ophthalmologic apparatus of the third aspect, further comprising: a moving-image acquiring optical system configured to acquire a moving image of the anterior eye part of the eye, wherein a part of its optical path is shared with the examination optical system; a projecting optical system configured to project a target for executing position matching of the examination optical system with the eye onto the eye; and an operation part, wherein when the characteristic position has not been specified by the characteristic position specifying part, the controller controls the projecting optical system to project the target onto the eye, controls the moving-image acquiring optical system to acquire a moving image of the anterior eye part onto which the target is being projected, controls a display to display the acquired moving image, and controls the first driver to move the examination optical system in accordance with an operation carried out by using the operation part.

A fifth aspect is the ophthalmologic apparatus of the fourth aspect, wherein after the examination optical system is moved by using the operation part, the characteristic position specifying part specifies an image position in the moving image that corresponds to the characteristic part, and the controller displays information indicating the specified image position over the moving image.

A sixth aspect is the ophthalmologic apparatus of the third aspect, wherein the characteristic part is a center of a pupil or a corneal apex of the anterior eye part.

A seventh aspect is the ophthalmologic apparatus of the third aspect, comprising an operation part, wherein the controller displays at least one of the two or more photograph images on a display, and when the characteristic position has not been specified by the characteristic position specifying part, the three-dimensional position calculating part calculates the three-dimensional position of the characteristic part based on the positions of the two or more imaging parts and an image position designated in the displayed photograph image by using the operation part.

An eighth aspect is the ophthalmologic apparatus of the seventh aspect, wherein when the image position is designated in one of the two or more photograph images, the three-dimensional position calculating part specifies image positions in other photograph images that correspond to this designated image position and calculates the three-dimensional position of the characteristic part based on the positions of the two or more imaging parts, the designated image position and the specified image positions.

A ninth aspect is the ophthalmologic apparatus of the seventh aspect, wherein the controller analyzes the two or more photograph images to evaluate image quality of the photograph images and selects one photograph image based on the evaluation results of the image quality to display it on the display.

A tenth aspect is the ophthalmologic apparatus of the third aspect, comprising an operation part, wherein the characteristic position specifying part analyzes the two or more photograph images to specify one or more candidate positions of the characteristic position, the controller displays at least one of the two or more photograph images and candidate position information indicating the specified candidate positions on a display, and the three-dimensional position calculating part calculates the three-dimensional position of the characteristic part based on the positions of the two or more imaging parts and a candidate position corresponding to candidate position information that is designated by using the operation part from among the one or more candidate position information displayed.

An eleventh aspect is the ophthalmologic apparatus of the second aspect, wherein the controller comprises an optical system position obtaining part configured to obtain a current position of the examination optical system, and controls the first driver based on the obtained current position and the three-dimensional position of the eye obtained by the analyzer to move the examination optical system.

A twelfth aspect is the ophthalmologic apparatus of the second aspect, wherein the two or more imaging parts acquire moving images of the anterior eye part of the eye from different directions in parallel, the analyzer successively analyzes two or more frames acquired substantially simultaneously in this moving image acquisition to obtain the three-dimensional positions of the eye successively, and the controller successively controls the first driver based on the three-dimensional positions successively obtained to make the position of the examination optical system follow movement of the eye.

A thirteenth aspect is the ophthalmologic apparatus of the second aspect, wherein the driver comprises a second driver configured to move the supporting part, and the controller controls the second driver based on the analysis results of the two or more photograph images from the analyzer to move the supporting part.

A fourteenth aspect is the ophthalmologic apparatus of the thirteenth aspect, wherein the second driver moves the supporting part at least in a vertical direction.

A fifteenth aspect is the ophthalmologic apparatus of the thirteenth aspect, wherein the analyzer comprises a moving target position determining part configured to determine a moving target position of the supporting part based on the two or more photograph images and positions of the two or more imaging parts, and the controller controls the second driver so as to move the supporting part to the moving target position.

A sixteenth aspect is the ophthalmologic apparatus of the thirteenth aspect, wherein the controller controls the second driver so as to move the supporting part to a preset initial position when information indicating change of subjects is input.

A seventeenth aspect is the ophthalmologic apparatus of the thirteenth aspect, comprising an approach detector configured to detect a state in which the subject approaches the supporting part, wherein when the approach is detected, the controller controls the two or more imaging parts to execute substantially simultaneous photography.

An eighteenth aspect is the ophthalmologic apparatus of the thirteenth aspect, comprising: an inputting part configured for inputting identification information of a subject, and a first storage configured to store position information indicating a position of the examination optical system and/or a position of the supporting part applied in an examination wherein the position information is associated with the identification information of a subject concerned, wherein when identification information is input by the inputting part, the controller obtains position information associated with this identification information from the first storage, and controls the first driver and/or the second driver so as to move the examination optical system and/or the supporting part to the position indicated in the obtained position information.

A nineteenth aspect is the ophthalmologic apparatus of the thirteenth aspect, comprising a contact detector configured to detect a state in which the face of the subject contacts with the supporting part, wherein while the contact is being detected, the controller is capable of controlling the first driver only from among the first driver and the second driver.

A twentieth aspect is the ophthalmologic apparatus of the nineteenth aspect, while the contact is not being detected, the controller is capable of controlling both of the first driver and the second driver.

A twenty-first aspect is the ophthalmologic apparatus of the thirteenth aspect, comprising a judging part configured to analyze a photograph image acquired by at least one of the two or more imaging parts to judge whether or not an image of the anterior eye part is included in a preset region in this photograph image, wherein the controller controls the first driver when the image of the anterior eye part is included in the preset region, and controls the second driver when the image of the anterior eye part is not included in the preset region.

A twenty-second aspect is the ophthalmologic apparatus of the first aspect, wherein each of the two or more imaging parts comprises an optical system, further comprising a second storage configured to previously store aberration information relating distortion aberration occurring in photograph images due to the optical system for each of the two or more imaging parts, wherein the analyzer comprises a correction part configured to correct distortion of each of the two or more photograph images based on the aberration information, and obtains the three-dimensional position of the eye based on the two or more photograph images corrected.

A twenty-third aspect is the ophthalmologic apparatus of the twenty-second aspect, wherein the aberration information is generated, for each of the two or more imaging parts, by analyzing multiple photograph images acquired by photographing reference points using a concerned imaging part while changing its position relative to the reference points.

A twenty-fourth aspect is the ophthalmologic apparatus of the first aspect, comprising: a photography moving part configured to move at least one of the two or more imaging parts; and a judging part configured to analyze a photograph image acquired by at least one of the two or more imaging parts to judge whether or not an image of the anterior eye part is included in a preset region in this photograph image, wherein when the image of the anterior eye part is not included in the preset region, the controller controls the photography moving part to move at least one of the two or more imaging parts in a direction away from the supporting part and/or a direction away from an optical axis of the examination optical system, and after at least one of the two or more imaging parts are moved, the judging part executes the judgment again.

A twenty-fifth aspect is the ophthalmologic apparatus of the first aspect, comprising a judging part configured to analyze a photograph image acquired by at least one of the two or more imaging parts to judge whether or not an image of the anterior eye part is included in a preset region in this photograph image, wherein when the image of the anterior eye part is not included in the preset region, the controller controls an output part to output warning information.

A twenty-sixth aspect is the ophthalmologic apparatus of the first aspect, comprising an image synthesis part configured to form a synthetic image of the two or more photograph images.

A twenty-seventh aspect is the ophthalmologic apparatus of the twenty-sixth aspect, wherein the controller displays the synthetic image on a display.

A twenty-eighth aspect is the ophthalmologic apparatus of the first aspect, wherein the controller displays at least one of the two or more photograph images on a display.

A twenty-ninth aspect is the ophthalmologic apparatus of the first aspect, wherein the two or more imaging parts comprises two cameras provided at different positions that are deviated from an optical path of the examination optical system.

A thirtieth aspect is the ophthalmologic apparatus of the first aspect, wherein the two or more imaging parts are provided at lower positions than an optical axis of the examination optical system.

A thirty-first aspect is the ophthalmologic apparatus of the second aspect, further comprising: a moving-image acquiring optical system configured to acquire a moving image of the anterior eye part of the eye, wherein a part of its optical path is shared with the examination optical system; a projecting optical system configured to project a target for executing position matching of the examination optical system with the eye onto the eye; and an operation part, wherein the controller controls the projecting optical system to project the target onto the eye, controls the moving-image acquiring optical system to acquire a moving image of the anterior eye part onto which the target is being projected, controls a display to display the acquired moving image, obtains relative position information indicating a relative position between the eye and the examination optical system based on the three-dimensional position obtained by the analyzer, displays the obtained relative position information on the display, and controls the first driver to move the examination optical system in accordance with an operation carried out by using the operation part.

A thirty-second aspect is the ophthalmologic apparatus of the thirty-first aspect, wherein the relative position information includes relative positions in an optical-axis direction of the examination optical system and horizontal and vertical directions that are perpendicular to the optical-axis direction.

A thirty-third aspect is the ophthalmologic apparatus of the thirty-second aspect, wherein the controller indicates the relative position in the optical-axis direction with a preset display color.

A thirty-fourth aspect is the ophthalmologic apparatus of the thirty-first aspect, comprising a storage configured to store measurement information of characteristics of the eye acquired in advance, wherein the controller obtains the relative position information based on the three-dimensional position and the measurement information.

A thirty-fifth aspect is the ophthalmologic apparatus of the first aspect, comprising filters configured to intercept light of wavelengths other than those of environmental illumination, wherein the filters are arranged at positions between the two or more imaging parts and the eye.

A thirty-sixth aspect is an ophthalmologic apparatus comprising: an examination optical system configured for carrying out an examination of an eye; a driver configured to move the examination optical system three-dimensionally; two or more imaging parts configured to substantially simultaneously photograph an anterior eye part of the eye from different directions; an analyzer configured to obtain a three-dimensional position of the eye by analyzing two or more photograph images acquired by the two or more imaging parts substantially simultaneously; and a controller configured to control the driver based on the three-dimensional position so as to align an optical axis of the examination optical system with an axis of the eye and adjust a distance between the eye and the examination optical system to a preset working distance.

It should be noted that it is possible to combine any of the configurations of the plurality of claims described above.

Effect of the Invention

According to the present invention, it is possible to preferably execute position matching between an eye and optical system.

MODES FOR CARRYING OUT THE INVENTION

Embodiments of ophthalmologic apparatuses related to the present invention are explained in detail with reference to drawings. Ophthalmologic apparatuses related to the present invention are used for optical examinations of an eye. Such ophthalmologic apparatuses include ophthalmologic imaging apparatuses and ophthalmologic measuring apparatuses as mentioned above. Examples of ophthalmologic imaging apparatuses include an OCT apparatus, a retinal camera, a scanning laser ophthalmoscope, a slit lamp, etc. Moreover, examples of ophthalmologic measuring apparatuses include an eye refractivity examination apparatus, a tonometer, a specular microscope, a wave-front analyzer, etc. Cases of applying the present invention to an optical coherence tomography apparatus are explained in the following embodiments; however, the present invention may be applied to any other ophthalmologic apparatuses.

In this specification, an image obtained by OCT is sometimes referred to as an OCT image. Further, a measuring action for forming an OCT image is sometimes referred to as an OCT measurement. It should be noted that the contents of the documents cited in this specification may be employed in the following embodiments.

In the following embodiments, an OCT apparatus using OCT of so-called spectral domain type is described; however, the present invention may also be applied to OCT apparatus using other types than spectral domain, such as swept source type and en-face type. It should be noted that the swept source OCT is a method of imaging the morphology of an object by: scanning (sweeping) the wavelength of light that is irradiated to the object; acquiring the spectral intensity distribution by successively detecting interference light obtained from superposing the reflected lights of the light of the respective wavelengths on reference light; and executing Fourier transform on the acquired spectral intensity distribution. The en-face OCT is a method of irradiating light with a predetermined beam diameter to an object and analyzing the components of interference light obtained from superposing the reflected light thereof and reference light, thereby forming an image of a cross-section of the object orthogonal to the travelling direction of the light, and it is also referred to as full-field type.

An apparatus that is configured by combining an OCT apparatus and a retinal camera is explained in the following embodiment; however, the scope in which the present invention is applicable is not limited to such a combination apparatus. The present invention may be applied to an ophthalmologic apparatus with a single function (for example, a retinal camera).

First Embodiment

Configuration

Figure 1:
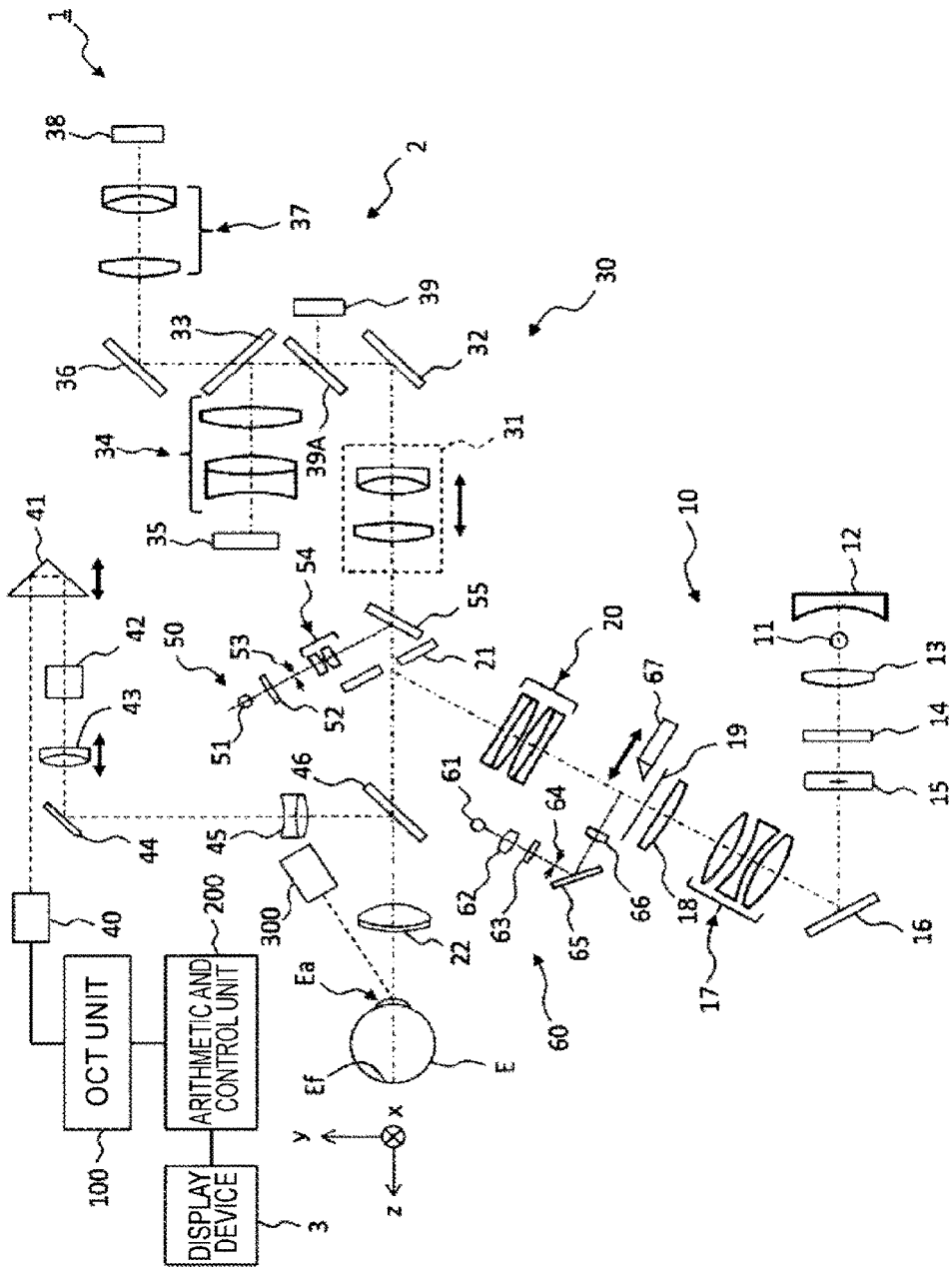
FIG. 1 is a schematic diagram illustrating an example of a configuration of an ophthalmologic apparatus according to an embodiment.

As shown in FIG. 1, an ophthalmologic apparatus 1 comprises a retinal camera unit 2, an OCT unit 100, and an arithmetic and control unit 200. The retinal camera unit 2 has almost the same optical system as a conventional retinal camera. The OCT unit 100 is provided with an optical system for obtaining an OCT image of a fundus. The arithmetic and control unit 200 is provided with a computer that executes various arithmetic processes, control processes, and so on.

[Retinal Camera Unit]

The retinal camera unit 2 shown in FIG. 1 is provided with an optical system for forming a two-dimensional image (fundus image) representing the surface morphology of the fundus Ef of the eye E. Fundus images include observation images, captured images, etc. The observation image is, for example, a monochrome moving image formed at a prescribed frame rate using near-infrared light. It should be noted that when the optical system is focused on the anterior eye part Ea of the eye E, the retinal camera unit 2 may obtain an observation image of the anterior eye part Ea. The optical system for acquiring moving images of the anterior eye part Ea corresponds to an example of a "moving-image acquiring optical system". The captured image is, for example, a color image captured by flashing visible light, or a monochrome still image using near-infrared light or visible light as illumination light. The retinal camera unit 2 may be configured to be capable of acquiring other types of images such as a fluorescein angiography image, an indocyanine green fluorescent image and a fundus autofluorescent image.

A chin rest and forehead rest for supporting the face of the subject is provided with the retinal camera unit 2. The chin rest and forehead rest correspond to the supporting part 440 indicated in FIG. 4A and FIG. 4B. It should be noted that, in FIG. 4A and FIG. 4B, symbol 410 indicates a base in which a drive system such as an optical system driver 2A, etc. and arithmetic and control circuits are accommodated. Moreover, symbol 420 indicates a case in which optical systems are accommodated, which is provided on the base 410. Moreover, symbol 430 indicates a lens case in which an objective lens 22 is accommodated, which is provided as a protrusion from the front surface of the case 420.

The retinal camera unit 2 is provided with an illumination optical system 10 and an imaging optical system 30. The illumination optical system 10 irradiates an illumination light to the fundus Ef. The imaging optical system 30 guides a fundus reflected light of the illumination light to imaging devices (CCD image sensors (sometimes simply called CCD) 35, 38). Moreover, the imaging optical system 30 guides signal light coming from the OCT unit 100 to the fundus Ef, and guides the signal light propagated through the fundus Ef to the OCT unit 100.

An observation light source 11 of the illumination optical system 10 comprises, for example, a halogen lamp. Light output from the observation light source 11 (observation illumination light) is reflected by a reflection mirror 12 with a curved reflection surface, and becomes near-infrared after passing through a visible cut filter 14 via a condenser lens 13. Further, the observation illumination light is once converged near an imaging light source 15, reflected by a mirror 16, and passes through relay lenses 17, 18, diaphragm 19, and relay lens 20. Then, the observation illumination light is reflected on the peripheral part (the surrounding region of an aperture part) of an aperture mirror 21, penetrates a dichroic mirror 46, and refracted by an object lens 22, thereby illuminating the fundus Ef. It should be noted that an LED (light emitting diode) may be used as the observation light source.

The fundus reflection light of the observation illumination light is refracted by the object lens 22, penetrates the dichroic mirror 46, passes through the aperture part formed in the center region of the aperture mirror 21, passes through a dichroic mirror 55, travels through a focusing lens 31, and is reflected by a mirror 32. Further, the fundus reflection light passes through a half-mirror 39A, is reflected by a dichroic mirror 33, and forms an image on the light receiving surface of the CCD image sensor 35 by a condenser lens 34. The CCD image sensor 35 detects, for example, the fundus reflection light at a preset frame rate. An image (observation image) based on the fundus reflection light detected by the CCD image sensor 35 is displayed on a display device 3. It should be noted that when the imaging optical system 30 is focused on the anterior eye part, an observation image of the anterior eye part of the eye E is displayed.

The imaging light source 15 is configured, for example, by a xenon lamp. Light output from the imaging light source 15 (imaging illumination light) is irradiated to the fundus Ef via a route that is similar to the observation illumination light. The fundus reflection light of the imaging illumination light is guided to the dichroic mirror 33 via the same route as that of the observation illumination light, passes through the dichroic mirror 33, is reflected by a mirror 36, and forms an image on the light receiving surface of the CCD image sensor 38 by a condenser lens 37. An image (captured image) based on the fundus reflection light detected by the CCD image sensor 38 is displayed on the display device 3. It should be noted that the display device 3 for displaying an observation image and the display device 3 for displaying a captured image may be the same or different. Further, when similar photographing is carried out by illuminating the eye E with infrared light, an infrared captured image is displayed. Moreover, an LED may be used as the imaging light source.

An LCD (Liquid Crystal Display) 39 displays a fixation target or a visual target for measuring visual acuity. The fixation target is a visual target for fixating the eye E, and is used when photographing a fundus or OCT measurement.

Part of the light output from the LCD 39 is reflected by a half-mirror 39A, reflected by the mirror 32, travels through the focusing lens 31 and the dichroic mirror 55, passes through the aperture part of the aperture mirror 21, penetrates the dichroic mirror 46, and is refracted by the object lens 22, thereby being projected to the fundus Ef.

By changing a display position of the fixation target on the screen of the LCD 39, a fixation position of the eye E is changed. Examples of the fixation position of the eye E includes a position for acquiring an image centered on the macula of the fundus Ef, a position for acquiring an image centered on the optic papilla, a position for acquiring an image centered on the fundus center between the macula and the optic papilla, etc. as in conventional retinal cameras, for example. Moreover, it is possible to arbitrarily change the display position of the fixation target.

Further, as with conventional retinal cameras, the retinal camera unit 2 is provided with an alignment optical system 50 and a focus optical system 60. The alignment optical system 50 generates a target (alignment target) for position matching of the optical system with respect to the eye E (alignment). The configuration for projecting the alignment target onto the eye corresponds to an example of "projecting optical system". The focus optical system 60 generates a target (split target) for adjusting the focus with respect to the eye E.

Light output from the LED 51 of the alignment optical system 50 (alignment light) travels through diaphragms 52, 53 and a relay lens 54, is reflected by the dichroic mirror 55, passes through the aperture part of the aperture mirror 21, penetrates the dichroic mirror 46, and is projected onto the cornea of the eye E by the object lens 22.

Cornea reflection light of the alignment light travels through the object lens 22, the dichroic mirror 46 and the abovementioned aperture part, and part of the cornea reflection light penetrates the dichroic mirror 55, passes through the focusing lens 31, is reflected by the mirror 32, penetrates the half-mirror 39A, is reflected by the dichroic mirror 33, and is projected onto the light receiving surface of the CCD image sensor 35 by the condenser lens 34. An image captured by the CCD image sensor 35 (alignment target) is displayed on the display device 3 along with the observation image. A user conducts alignment by an operation that is the same as conventional retinal cameras. Instead, alignment may be performed in such a way that an arithmetic and control unit 200 analyzes the position of the alignment target to move the optical system (automatic alignment). It should be noted that, in the present embodiment, automatic alignment is possible using anterior eye cameras 300 (mentioned later); therefore, the ability of automatic alignment using the alignment target is not necessarily required. However, it is possible to configure it such that automatic alignment may be carried out using the alignment target when automatic alignment using the anterior eye cameras 300 fails or the like, or to configure it such that automatic alignment using the anterior eye cameras 300 and automatic alignment using the alignment target may be selectively used.

In order to conduct focus adjustment, the reflection surface of a reflection rod 67 is arranged in a slanted position in the light path of the illumination optical system 10. Light output from an LED 61 of the focus optical system 60 (focus light) passes through a relay lens 62, is split into two light fluxes by a split target plate 63, passes through a two-hole diaphragm 64, is reflected by a mirror 65, and is reflected after an image is formed once on the reflection surface of the reflection rod 67 by a condenser lens 66. Further, the focus light travels through the relay lens 20, is reflected by the aperture mirror 21, penetrates the dichroic mirror 46, and is refracted by the object lens 22, thereby being projected on the fundus Ef.

The fundus reflection light of the focus light passes through the same route as the cornea reflection light of the alignment light and is detected by the CCD image sensor 35. An image captured by the CCD image sensor 35 (split target) is displayed on the display device 3 along with an observation image. The arithmetic and control unit 200, as in the conventional case, analyzes the position of the split target, and moves the focusing lens 31 and the focus optical system 60 for focusing (automatic focusing). It should be noted that focusing may be performed manually while visually recognizing the split target.

The dichroic mirror 46 branches the optical path for OCT measurement from the optical path for fundus photography. The dichroic mirror 46 reflects light of the wavelength band used in OCT measurement and transmits light for fundus photography. This optical path for OCT measurement is provided with, in order from the OCT unit 100 side, a collimator lens unit 40, an optical-path-length changing part 41, a galvano scanner 42, a focusing lens 43, a mirror 44, and a relay lens 45.

The optical-path-length changing part 41 is movable in the direction of the arrow indicated in FIG. 1, thereby changing the length of the optical path for OCT measurement. This change in the optical path length is used for correcting the optical path in accordance with the axial length of the eye E, adjusting the interference state, etc. The optical-path-length changing part 41 is configured to include, for example, a corner cube and a mechanism for moving this.

The galvano scanner 42 changes the travelling direction of light (signal light LS) travelling along the optical path for OCT measurement. Thereby, the fundus Ef may be scanned using the signal light LS. The galvano scanner 42 is configured to include, for example, a galvano mirror for scanning with the signal light LS in the x direction, a galvanometer mirror for scanning in the y direction, and a mechanism for independently driving these. Accordingly, the signal light LS may be scanned in any direction on the xy plane.

Figure 4A:
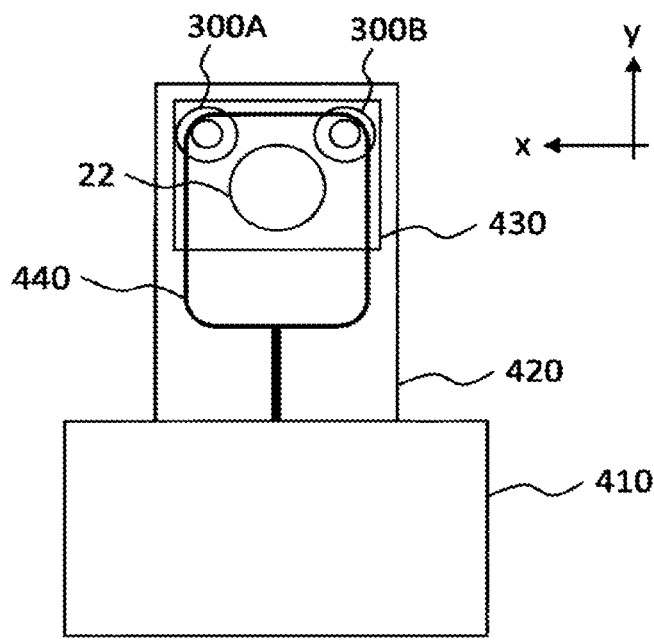
FIG. 4A is a schematic diagram illustrating an example of a configuration of an ophthalmologic apparatus according to an embodiment.
Figure 4B:
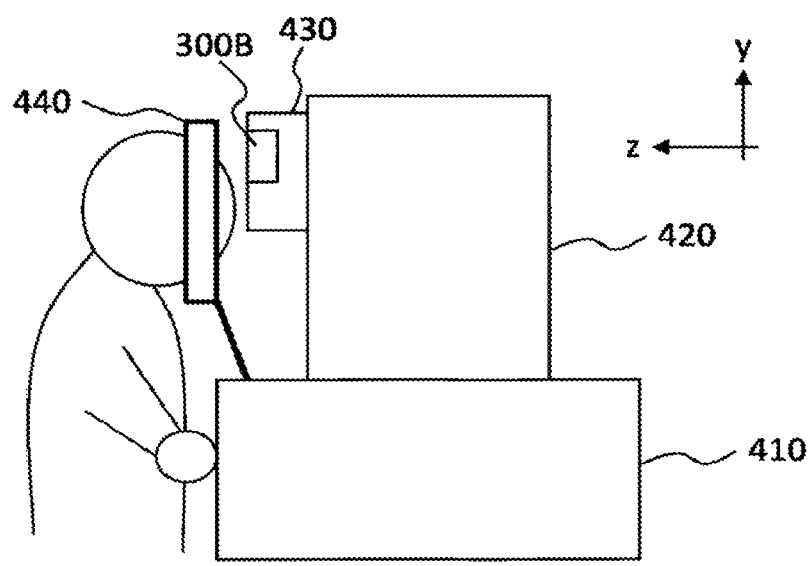
FIG. 4B is a schematic diagram illustrating an example of a configuration of an ophthalmologic apparatus according to an embodiment.

The retinal camera unit 2 is provided with anterior eye cameras 300. The anterior eye cameras 300 substantially simultaneously photograph an anterior eye part Ea from different directions. In the present embodiment, two cameras are provided on the surface of the retinal camera unit 2 of the subject side (refer to the anterior eye cameras 300A and 300B indicated in FIG. 4A). Moreover, the anterior eye cameras 300A and 300B are, as indicated in FIG. 1 and FIG. 4A, provided in positions away from the optical path of an illumination optical system 10 and the optical path of an imaging optical system 30. Hereinafter, the two anterior eye cameras 300A and 300B may be collectively represented by the symbol 300.

In the present embodiment, two anterior eye cameras 300A and 300B are provided; however, the number of anterior eye cameras in the present invention may be any number of two or more. However, when taking into consideration the arithmetic process (mentioned later), it is sufficient that a configuration is capable of substantially simultaneously photographing the anterior eye part from two different direction. Moreover, in the present embodiment, the anterior eye camera 300 is separately provided from the illumination optical system 10 and imaging optical system 30; however, the similar anterior-eye photography may be performed using at least the imaging optical system 30. That is, one from among two or more anterior eye cameras may be a configuration comprising the imaging optical system 30. In any case, it is sufficient in the present embodiment that the anterior eye part may be substantially simultaneously photographed from two (or more) different directions.

It should be noted that "substantially simultaneous" indicates allowing a time lag of the photographing timings by a degree of being able to ignore eye movements when photographing using two or more anterior eye cameras. Accordingly, images in which the eye E is in substantially the same position (direction) may be acquired by the two or more anterior eye cameras.

Moreover, photographing using the two or more anterior eye cameras may be a moving image photographing or a still image photographing; however, in the present embodiment, a case of carrying out moving image photographing is explained in greater detail. In the case of moving image photographing, substantial and simultaneous photographing of the anterior eye part mentioned above may be realized by means of controlling to match the timings for commencing photographing, or controlling frame rates and/or the timings for capturing respective frames. Meanwhile, in the case of still image photographing, this may be realized by controlling so as to match the timings for photographing.

[OCT Unit]

Figure 2:
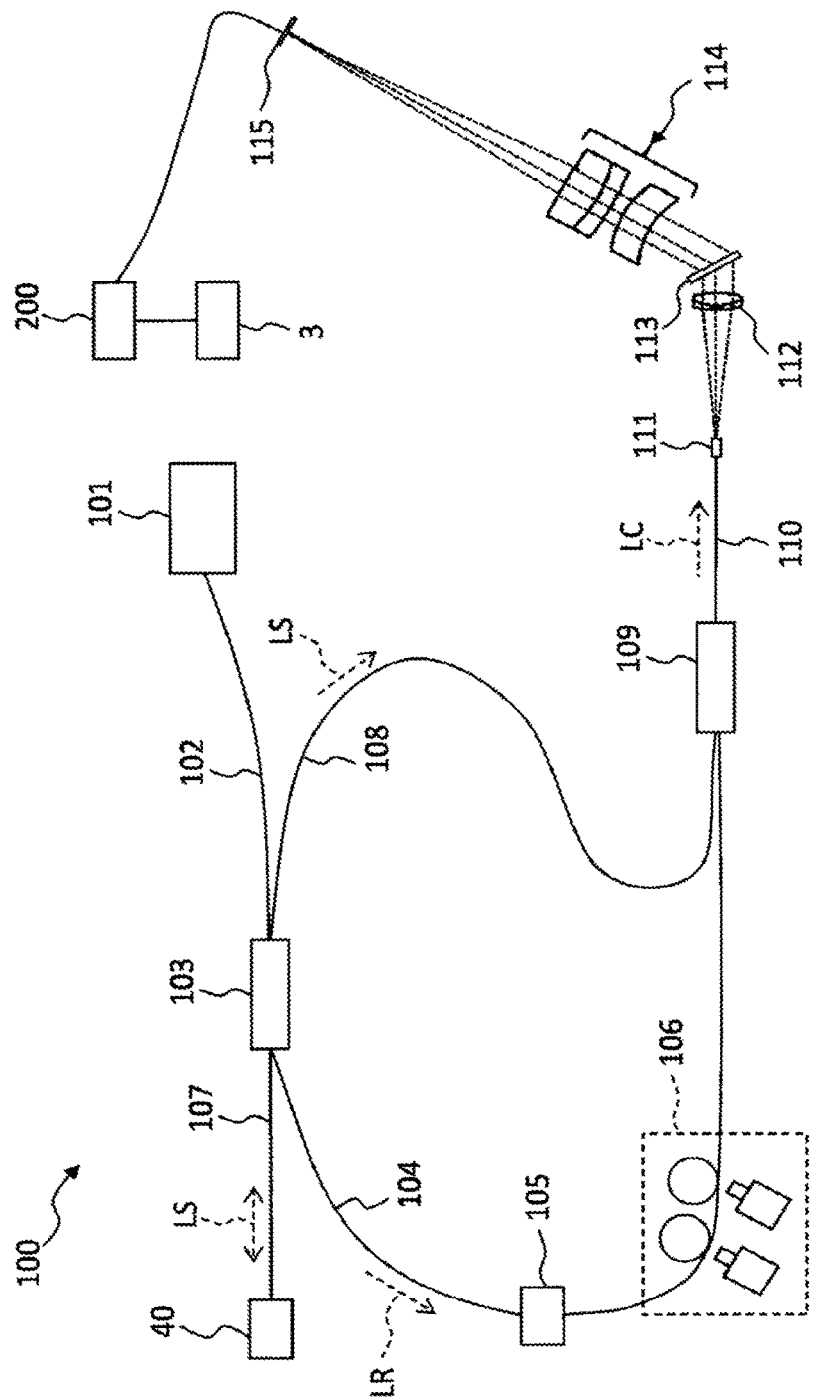
FIG. 2 is a schematic diagram illustrating an example of a configuration of an ophthalmologic apparatus according to an embodiment.

The configuration of the OCT unit 100 will be described with reference to FIG. 2. The OCT unit 100 is provided with an optical system for obtaining an OCT image of the fundus Ef. The optical system has a similar configuration to a conventional Fourier-domain-type OCT apparatus. That is to say, the optical system is configured to split low-coherence light into reference light and signal light, make the signal light propagated through a fundus and the reference light propagated through a reference optical path interfere with each other to generate interference light, and detect the spectral component of this interference light. This detection result (detection signal) is transmitted to the arithmetic and control unit 200.

It should be noted that, in the case of swept source type OCT apparatus, a wavelength sweeping light source (swept source) is provided instead of a light source outputting low-coherence light, while an optical element for spectrally decomposing interference light is not provided. Generally, regarding the configuration of the OCT unit 100, known technologies may be applied according to the type of OCT.

The light source unit 101 outputs a broadband, low-coherence light L0. The low-coherence light L0 includes, for example, a near-infrared wavelength band (approximately 800 nm to 900 nm), and has a temporal coherence length of around several tens of micrometers. It should be noted that, a wavelength band that is not visible to human eyes, such as near-infrared light with a central wavelength of around 1040 to 1060 nm, for example, may be used as the low-coherence light L0.

The light source unit 101 is configured to include light output device, such as an SLD (super luminescent diode), LED, SOA (Semiconductor Optical Amplifier) and the like.

The low coherence light L0 output from the light source unit 101 is guided to a fiber coupler 103 by an optical fiber 102 and split into signal light LS and reference light LR.

The reference light LR is guided by the light fiber 104 and arrives at an optical attenuator (attenuator) 105. The optical attenuator 105 automatically adjusts the light amount of the reference light LR guided by the light fiber 104 under the control of the arithmetic and control unit 200 using known technologies. The reference light LR with the light amount having adjusted by the optical attenuator 105 is guided by the light fiber 104, arriving at a polarization adjuster (polarization controller) 106. The polarization adjuster 106 is an apparatus that, by means of applying external stress to a looped light fiber 104, adjusts the polarization condition of the reference light LR guided in the light fiber 104. It should be noted that the configuration of the polarization adjuster 106 is not limited to this and any known technologies may be used. The reference light LR with adjusted polarization condition by the polarization adjuster 106 arrives at the fiber coupler 109.

The signal light LS generated by the fiber coupler 103 is guided by the light fiber 107 and becomes a parallel light flux by means of the collimator lens unit 40. Further, the signal light LS arrives at the dichroic mirror 46 via the optical-path-length changing part 41, the galvano scanner 42, the focusing lens 43, the mirror 44, and the relay lens 45. Subsequently, the signal light LS is reflected by the dichroic mirror 46, refracted by the objective lens 22, and projected onto the fundus Ef. The signal light LS is scattered (including reflections) at various depth positions of the fundus Ef. A back-scattered light of the signal light LS from the fundus Ef reversely advances along the same path as the outward path and is guided to the fiber coupler 103, arriving at the fiber coupler 109 via the light fiber 108.

The fiber coupler 109 causes the back-scattered light of the signal light LS and the reference light LR having passed through the optical fiber 104 to interfere with each other. Interference light LC thus generated is guided by an optical fiber 110 and output from an exit end 111. Further, the interference light LC is converted to a parallel light flux by a collimator lens 112, spectrally divided (spectrally decomposed) by a diffraction grating 113, converged by the convergence lens 114, and projected onto the light receiving surface of a CCD image sensor 115. It should be noted that although the diffraction grating 113 shown in FIG. 2 is of the transmission type, it is possible to use a spectrally decomposing element of any other type, such as a diffraction grating of reflection type.

The CCD image sensor 115 is for example a line sensor, and detects the respective spectral components of the spectrally decomposed interference light LC and converts the components into electric charges. The CCD image sensor 115 accumulates these electric charges to generate a detection signal, and transmits the signal to the arithmetic and control unit 200.

Although a Michelson-type interferometer is employed in this embodiment, it is possible to employ any type of interferometer such as a Mach-Zehnder-type as necessary. Instead of a CCD image sensor, other types of image sensors, such as a CMOS (Complementary Metal Oxide Semiconductor) image sensor, can be used.

[Arithmetic and Control Unit]

A configuration of the arithmetic and control unit 200 will be described. The arithmetic and control unit 200 analyzes the detection signals input from the CCD image sensor 115 to form an OCT image of the fundus Ef. An arithmetic process for this is the same as that of a conventional Fourier-domain-type OCT apparatus.

Further, the arithmetic and control unit 200 controls each part of the retinal camera unit 2, the display device 3 and the OCT unit 100. For example, the arithmetic and control unit 200 causes the display device 3 to display an OCT image G of the fundus Ef.

Moreover, as control of the retinal camera unit 2, the arithmetic and control unit 200 executes: control of actions of the observation light source 11, the imaging light source 15 and the LED's 51 and 61; control of action of the LCD 39; control of movements of the focusing lenses 31 and 43; control of movement of the reflection rod 67; control of movement of the focus optical system 60; control of movement of the optical path length changing part 41; control of action of the galvano scanner 42; control of actions of the anterior eye cameras 300; and so on.

Further, as control of the OCT unit 100, the arithmetic and control unit 200 executes: control of action of the light source unit 101; control of action of the optical attenuator 105; control of action of the polarization adjuster 106; control of action of the CCD image sensor 115; and so on.

The arithmetic and control unit 200 includes a microprocessor, a RAM, a ROM, a hard disk drive, a communication interface, and so on, as in conventional computers. The storage device such as a hard disk drive stores computer programs for controlling the ophthalmologic apparatus 1. The arithmetic and control unit 200 may be provided with various kinds of circuit boards, such as a circuit board for forming OCT images. Moreover, the arithmetic and control unit 200 may be provided with operation devices (input devices) such as a keyboard and a mouse, and/or display devices such as an LCD.

The retinal camera unit 2, the display device 3, the OCT unit 100, and the arithmetic and control unit 200 may be integrally configured (that is, within a single case), or configured as two of more separated cases.

[Control System]

A configuration of a control system of the ophthalmologic apparatus 1 will be described with reference to FIG. 3.

(Controller)

The control system of the ophthalmologic apparatus 1 has a configuration with a controller 210 as a center. The controller 210 includes, for example, the aforementioned microprocessor, RAM, ROM, hard disk drive, and communication interface. The controller 210 is provided with a main controller 211, a storage 212 and an optical system position obtaining part 213.

(Main Controller)

The main controller 211 carries out various kinds of controls mentioned above. It should be noted that the movement control of the focusing lens 31 is configured to control a focus driver (not illustrated) to move the focusing lens 31 in the optical-axis direction. Thereby, the focus position of the imaging optical system 30 is changed. Moreover, the main controller 211 is capable of controlling the optical system driver 2A to three-dimensionally move the optical system installed in the retinal camera unit 2.

This control is carried out upon automatic alignment and/or tracking. Here, tracking refers to moving the optical system of the apparatus in accordance with the eye movement of the eye E. Tracking is carried out at, for example, the stage after alignment (depending on the conditions, focusing is also carried out in advance). Tracking is a function causing the position of the optical system of the apparatus to follow the eye movement, thereby maintaining a suitable positional relationship in which alignment (and focusing) is matched.

It should be noted that the optical system driver 2A of the present embodiment moves the optical system installed in the retinal camera unit 2; however, a configuration is possible in which the optical system installed in the retinal camera unit 2 and the optical system installed in the OCT unit 100 are moved by means of the optical system driver 2A. The optical system driver 2A is an example of a "first driver."

Moreover, the anterior eye cameras 300 of the present embodiment are provided on the case of the retinal camera unit 2; accordingly, the anterior eye cameras 300 can be moved by means of controlling the optical system driver 2A. This optical system driver 2A functions as an example of a "photography moving part". Moreover, it is possible to provide a camera moving part capable of independently moving the two or more anterior eye cameras 300, respectively. Specifically, the camera moving part may be configured to include driving mechanisms (actuator, power transmission mechanism, etc.) provided with respect to each anterior eye camera 300. Moreover, the camera moving part may be configured to move two or more anterior eye cameras 300 by transmitting the power generated by a single actuator by means of the power transmission mechanism provided for each anterior eye camera 300.

The main controller 211 executes a process of writing data into the storage 212, and a process of reading out data from the storage 212.

(Storage)

The storage 212 stores various kinds of data. The data stored in the storage 212 is, for example, image data of OCT images, image data of fundus images, and eye information. The eye information includes information on a subject such as a patient ID and a name, information on an eye such as identification information of left eye or right eye, and so on. Moreover, various kinds of programs and data in order to operate the ophthalmologic apparatus 1 are stored in the storage 212.

In particular, aberration information 212a is stored in the storage 212 in advance. The aberration information 212a includes information, for each anterior eye camera 300, regarding the distortion aberration occurring in a photograph image due to effects by the optical system installed therein. Here, the optical system installed in the anterior eye camera 300 includes, for example, optical elements occurring distortion aberration of lenses, etc. It may be said that the aberration information 212a is a parameter that quantifies the deformation of the photograph images caused by these optical elements.

An example of a method for generating the aberration information 212a is explained. Taking into consideration instrumental error (difference in distortion aberration) of the anterior eye cameras 300, the following measurements are carried out for each anterior eye camera 300. An operator prepares reference points. The reference points are photographing target used in detecting the distortion aberration. The operator performs photographing multiple times while changing the relative position between the reference points and the anterior eye cameras 300. Accordingly, multiple photograph images of the reference points photographed from different directions may be obtained. The operator analyzes the multiple acquired photograph images, thereby generating the aberration information 212a of this anterior eye camera 300. It should be noted that the computer that performs this analysis process may be an image processor 230 or any other computer (computer for inspection before shipping products, computer for maintenance, etc.).

The analysis processes for generating the aberration information 212a include, for example, the following procedures:

an extraction procedure for extracting image regions corresponding to the reference points in each photograph image;

a distribution state calculating procedure for calculating the distribution state (coordinates) of the image regions corresponding to the reference points in each photograph image;

a distortion aberration calculating procedure for calculating a parameter indicating the distortion aberration based on the obtained distribution state; and a correction factor calculating procedure for calculating a factor for correcting the distortion aberration based on the obtained parameter.

It should be noted that the parameter related to the distortion aberration that is given to an image by the optical system may include the principal distance, the position of a principal point (vertically and horizontally), the distortion of a lens (radiation direction and tangential direction), etc. The aberration information 212a is constructed as information (for example, table information) that associates the identification information of each anterior eye camera 300 and the correction factor corresponding thereto. The aberration information 212a generated in this manner is stored in the storage 212 by the main controller 211. Generation of such aberration information 212a and the aberration correction process based on this is referred to as camera calibration, etc.

(Optical System Position Obtaining Part)

The optical system position obtaining part 213 obtains the current position of the examination optical system installed in the ophthalmologic apparatus 1. The examination optical system is the optical system used for optically examining the eye E. The examination optical system in the ophthalmologic apparatus 1 of the present embodiment (combined machine of the retinal camera and OCT apparatus) is the optical system for obtaining images of an eye.

The optical system position obtaining part 213 receives information presenting the content of the movement control of the optical system driver 2A by means of the main controller 211, and obtains the current position of the examination optical system moved by the optical system driver 2A. A detailed example of this process will be explained. The main controller 211 controls the optical system driver 2A at a predetermined timing (upon start-up of the apparatus, upon inputting patient information, etc.) and moves the examination optical system to a predetermined initial position. Thereafter, the main controller 211 stores the control content each time the optical system driver 2A is controlled. Thereby, a history of the control contents may be obtained. The optical system position obtaining part 213 refers to this history and obtains the control contents to date, and determines the current position of the examination optical system based on these control contents.

Moreover, each time the main controller 211 controls the optical system driver 2A, the control contents thereof may be transmitted to the optical system position obtaining part 213, and the current position of the examination optical system may be obtained each time the optical system position obtaining part 213 receives the control contents.

As another configuration example, the position sensor detecting the position of the examination optical system may be provided with the optical system position obtaining part 213.

When the current position of the examination optical system is obtained by the optical system position obtaining part 213 as stated above, the main controller 211 is capable of, based on the obtained current position and the three-dimensional position of the eye E obtained by an analyzer 231 (mentioned later), causing the optical system driver 2A to move the examination optical system. Specifically, the main controller 211 recognizes the current position of the examination optical system from the acquisition result by the optical system position obtaining part 213, and recognizes the three-dimensional position of the eye E from the analysis result by the analyzer 231. Subsequently, in order that the position of the examination optical system with respect to the three-dimensional position of the eye E becomes a predetermined positional relationship, the main controller 211 changes the position thereof with the current position of the examination optical system as the starting point. This predetermined positional relationship may be such that the positions in the x and y directions respectively coincide, while the distance in the z direction becomes a predetermined working distance.

(Image Forming Part)

The image forming part 220 forms image data of a cross sectional image of the fundus Ef based on the detection signals from the CCD image sensor 115. Like the conventional spectral-domain-type OCT, this process includes processes such as noise elimination (noise reduction), filtering and FFT (Fast Fourier Transform). In the case of other types of OCT apparatus, the image forming part 220 executes known processes in accordance with the type thereof.

The image forming part 220 is configured to include, for example, the aforementioned circuit boards. It should be noted that "image data" and the "image" based on this may be identified with each other in this specification.

(Image Processor)

The image processor 230 executes various image processes and analysis on images formed by the image forming part 220. For example, the image processor 230 executes various correction processes such as luminance correction and dispersion compensation of images. Moreover, the image processor 230 executes various image processes and analysis on images (fundus images, anterior eye images, etc.) obtained by the retinal camera unit 2.

The image processor 230 executes known image processes such as an interpolation process of interpolating pixels between cross sectional images, thereby forming a three-dimensional image data of the fundus Ef. The three-dimensional image data refers to image data that the positions of pixels are defined by the three-dimensional coordinates. The three-dimensional image data is, for example, image data composed of three-dimensionally arranged voxels. This image data is referred to as volume data, voxel data, or the like. For displaying an image based on the volume data, the image processor 230 executes a rendering process (such as volume rendering and MIP (Maximum Intensity Projection)) on this volume data to form image data of a pseudo three-dimensional image taken from a predetermined view direction. This pseudo three-dimensional image is displayed on the display 240A.

Further, it is also possible to form stack data of multiple cross sectional images as a three-dimensional image data. Stack data is image data obtained by three-dimensionally arranging multiple cross sectional images obtained along multiple scanning lines, based on the positional relation of the scanning lines. That is to say, stack data is image data obtained by expressing multiple cross sectional images defined by originally individual two-dimensional coordinate systems by a three-dimensional coordinate system (namely, embedding into a three-dimensional space).

Further, the image processor 230 is provided with an analyzer 231, an image judging part 232, and an image synthesis part 233.

(Analyzer)

The analyzer 231 analyzes two or more photograph images substantially simultaneously obtained by two or more anterior eye cameras 300, thereby obtaining the three-dimensional position of the eye E. As an example of a configuration for performing this process, the analyzer 231 is provided with an image correction part 2311, a characteristic position specifying part 2312, and a three-dimensional position calculating part 2313.

(Image Correction Part)

The image correction part 2311 corrects the distortion of each photograph image obtained by the anterior eye cameras 300 based on the aberration information 212a stored in the storage 212. This process may be carried out by, for example, known image process technology based on a correction factor for correcting distortion aberration. The image correction part 2311 is an example of a "correction part". It should be noted that, for cases in which the distortion aberration caused in photograph images due to the optical system of the anterior eye cameras 300 is sufficiently small, etc., there is no need to provide the aberration information 212a and the image correction part 2311.

(Characteristic Position Specifying Part)

The characteristic position specifying part 2312 analyzes each photograph image (with the distortion aberration corrected by the image correction part 2311), thereby specifying the position in the photograph image corresponding to the predetermined characteristic part of the anterior eye part Ea (referred to as the characteristic position). As the predetermined characteristic part, for example, the center of the pupil or the corneal apex of the eye E may be used. Hereinafter, a specific example of a process for specifying the center of the pupil is explained.

First, the characteristic position specifying part 2312 specifies the image region (pupillary region) corresponding to the pupil of the eye E based on the distribution of the pixel values (luminous values, etc.) in a photograph image. Generally, the pupil is represented with lower luminance compared to other parts, so the pupillary region may be specified by searching an image region with low luminance. At this time, the pupillary region may be specified taking into consideration the shape of the pupil. That is, a configuration is possible of specifying the pupillary region by means of searching a substantially circular image region with low luminance.

Next, the characteristic position specifying part 2312 specifies the center position of the specified pupillary region. As mentioned above, the pupil is substantially circular; therefore, it is possible to specify the contour of the pupillary region, specify the center position of this contour (an approximate circle or an approximate ellipse thereof), and treat this as the center of the pupil. Instead, it is possible to derive the center of gravity of the pupillary region and treat this center of gravity as the center of the pupil.

It should be noted that even when specifying the characteristic position corresponding to other characteristic part, it is possible to specify the characteristic position based on the pixel value distribution of the photograph image in the same manner as those mentioned above.

(Three-Dimensional Position Calculating Part)

The three-dimensional position calculating part 2313 calculates the three-dimensional position of the eye E based on the positions of two or more anterior eye cameras 300 and the characteristic positions in the two or more photograph images specified by the characteristic position specifying part 2312. This process is explained with reference to FIG. 5A and FIG. 5B.

Figure 5A:
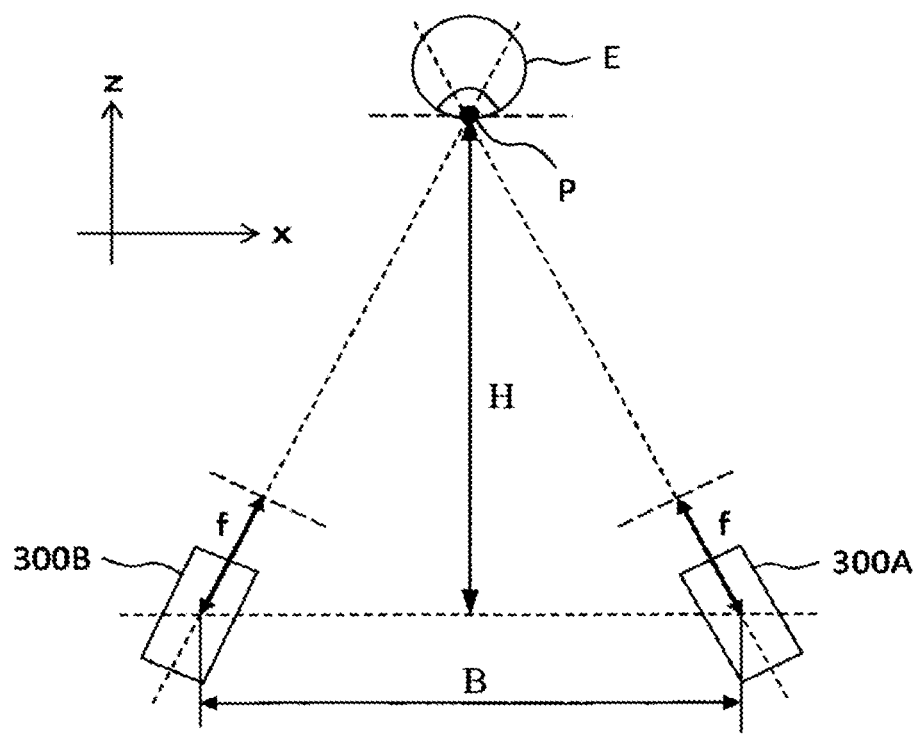
FIG. 5A is a schematic diagram for explaining processing executed by an ophthalmologic apparatus according to an embodiment.
Figure 5B:
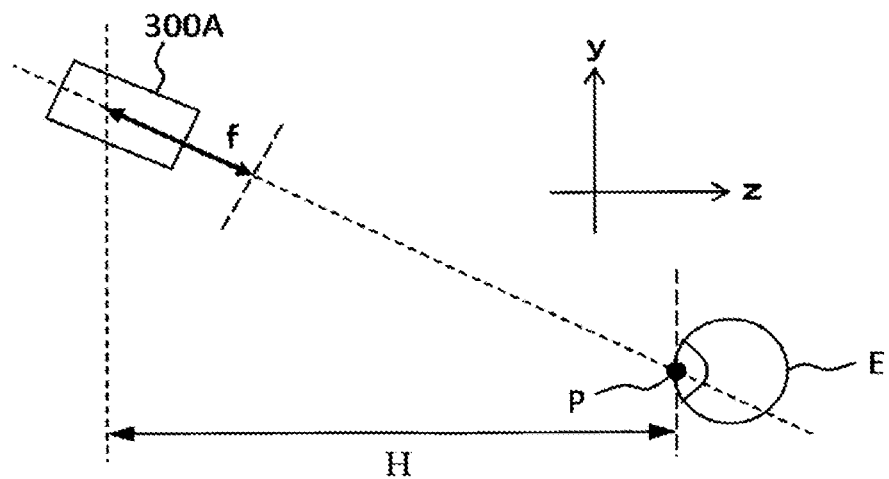
FIG. 5B is a schematic diagram for explaining processing executed by an ophthalmologic apparatus according to an embodiment.

FIG. 5A is a top view illustrating the positional relationship between the eye E and the anterior eye cameras 300A and 300B. FIG. 5B is a side view illustrating the positional relationship between the eye E and the anterior eye cameras 300A and 300B. The distance (base line length) between the two anterior eye cameras 300A and 300B is represented as "B." The distance (photographing distance) between the base line of the two anterior eye cameras 300A and 300B and a characteristic part P of the eye E is represented as "H." The distance (screen distance) between the respective anterior eye cameras 300A and 300B and a screen plane thereof is represented as "f."

In such an arrangement state, the resolution of images photographed by the anterior eye cameras 300A and 300B is expressed by the following formula. Here, $\Delta p$ represents the pixel resolution.

$xy$ resolution(planar resolution): $\Delta xy = H \times \Delta p / f$ $z$ resolution(depth resolution): $\Delta z = H \times H \times \Delta p / (B \times f)$ The three-dimensional position calculating part 2313 applies known trigonometry, taking into consideration the positional relationship indicated in FIG. 5A and FIG. 5B, to the positions of the two anterior eye cameras 300A and 300B (these are known) and the characteristic positions corresponding to the characteristic part P in the two photograph images, thereby calculating the three-dimensional position of the characteristic part P, that is, the three-dimensional position of the eye E.

The three-dimensional position of the eye E calculated by the three-dimensional position calculating part 2313 is transmitted to the controller 210. Based on this calculation result of the three-dimensional position, the controller 210 controls the optical system driver 2A such that the optical axis of the examination optical system matches the axis of the eye E and such that the distance of the examination optical system with respect to the eye E becomes the predetermined working distance. Here, the working distance is a preset value also referred to as the working distance, meaning the distance between the eye E and the examination optical system when performing examination using the examination optical system.

Moreover, when the anterior eye cameras 300 parallelly photograph moving images of the anterior eye part Ea from different directions, tracking of the examination optical system with respect to the movement of the eye E becomes possible by carrying out, for example, the following processes (1) and (2).

(1) The analyzer 231 successively analyzes the two or more frames substantially simultaneously obtained by photographing moving pictures using two or more anterior eye cameras 300, thereby successively obtaining the three-dimensional positions of the eye E.

(2) The controller 210 successively controls the optical system driver 2A based on the three-dimensional positions of the eye E successively obtained by the analyzer 231, thereby causing the position of the examination optical system to follow the movement of the eye E.

(Image Judging Part)

The image judging part 232 analyzes a photograph image(s) obtained by at least one from among two or more anterior eye cameras 300, thereby judging whether or not the image of the anterior eye part Ea is within the predetermined area in this photograph image(s).

This predetermined area is set in advance within the photographing region of the anterior eye camera 300, for example, set as a region including the center of this photographing region. Here, the range of this predetermined area may be changed in accordance with the photographing conditions of the anterior eye camera 300 (the position, the photographic magnification, etc. of the anterior eye camera 300). Moreover, the range of this predetermined area may be determined in accordance with the setting of a characteristic point (mentioned later). Moreover, the predetermined area may be set so as to correspond to the position of the supporting part 440 (chin rest, forehead rest, etc.; refer to FIG. 4A and FIG. 4B.) supporting the face of the subject or the vicinity position thereof. The image judging part 232 corresponds to an example of a "judging part".

A detailed example of the process carried out by the image judging part 232 is explained. First, the image judging part 232 specifies the image region corresponding to the predetermined characteristic point of the anterior eye part Ea from the photograph image. This characteristic point may be the center of the pupil, the contour of the pupil, the center of the iris, the contour of the iris, the corneal apex, etc. The process of specifying the image region corresponding to the characteristic point is carried out similarly to, for example, the process carried out by the characteristic position specifying part 2312. It should be noted that when the characteristic point and the characteristic part are the same, the specification result by the characteristic position specifying part 2312 may be used in the process carried out by the image judging part 232.

Next, the image judging part 232 judges whether or not the specified characteristic point is within the predetermined area of the photograph image (the frame thereof). This process may be carried out by comparing the coordinates corresponding to the predetermined area and the coordinates of the characteristic point.

The image judging part 232 transmits this determination result to the controller 210. When it is determined that the image of the anterior eye part Ea is not included in the predetermined area, the controller 210 controls the optical system driver 2A (camera moving part) to move the anterior eye cameras 300 in a direction away from the supporting part 440 (that is, the face of the subject) and/or a direction outwards of the supporting part 440. The direction away from the supporting part 440 is the −z direction in the coordinate system indicated in FIG. 1, etc. Moreover, the direction outwards of the supporting part 440 is the direction in which the anterior eye cameras 300 moves away from the optical axis of the examination optical system. The direction away from the examination optical system may be defined horizontally (±x direction) and/or vertically (±y direction). That is, the direction away from the examination optical system may be defined in any direction in the xy plane.

Moreover, the moving direction and/or the moving distance of the anterior eye camera 300 may be set based on, for example, the positional relationship between the anterior eye camera 300 and the supporting part 440 before movement. Moreover, a configuration is possible of alternately carrying out the determination process by the image judging part 232 and the moving process of the anterior eye camera 300, thereby controlling so as to improve the position of the anterior eye camera 300 toward a suitable position. Moreover, a configuration is possible of determining the moving direction and/or the moving distance of the anterior eye camera 300 in accordance with the distance (number of pixels) between the image region corresponding to the characteristic point and the predetermined area. Moreover, a configuration is possible of determining the moving direction and/or the moving distance of the anterior eye camera 300 in accordance with the distance between the image region corresponding to the characteristic point and the predetermined position (for example, the center position) in the predetermined area.

Other operation examples based on the determination result by the image judging part 232 are explained. When it is determined that the image of the anterior eye part Ea is not included in the predetermined area, the controller 210 causes an output part to output a predetermined warning information. This output part may be the display 240A, an audio output part (not illustrated), etc. When using the display 240A as the output part, the controller 210 causes the display 240A to display a warning message including a predetermined text string information, image information, pop-up window, etc. When the audio output part is used as the output part, the controller 210 causes the audio output part to output the predetermined voice information, warning sound, etc.

From such warning information, the user recognizes that the image of the anterior eye part Ea is not included in the predetermined area. Subsequently, the user can use the operation part 240B to three-dimensionally move the anterior eye camera 300. Further, the controller 210 may output information (movement information) indicating the moving direction and/or the moving distance of the anterior eye camera 300 together with a warning information. This movement information is generated based on, for example, the positional relationship between the image region corresponding to the characteristic point obtained by the image judging part 232 and the predetermined area. A configuration is possible wherein the determination process is carried out again by the image judging part 232 once the manual movement by the user is completed.

(Image Synthesis Part)

The image synthesis part 233 forms a synthetic image of the two or more photograph images that are substantially simultaneously obtained by two or more anterior eye cameras 300. A stereoscopic image and an image obtained from viewpoint conversion (viewpoint-converted image) based on the two or more photograph images are examples of the synthetic image. The viewpoint of the viewpoint-converted image is set on, for example, the optical axis of the examination optical system. These synthetic images may be obtained by using any known image synthesizing process.

The image processor 230 that functions as above includes, for example, the aforementioned microprocessor, RAM, ROM, hard disk drive, circuit board, and so on. Computer programs that cause a microprocessor to execute the above functions are previously stored in a storage device such as a hard disk drive.

(User Interface)

A user interface 240 includes the display 240A and the operation part 240B. The display 240A is configured including the aforementioned display device of the arithmetic and control unit 200 and the display device 3. The operation part 240B is configured including the aforementioned operation device of the arithmetic and control unit 200. The operation part 240B may include various kinds of buttons or keys provided on the case of the ophthalmologic apparatus 1 or its outside. For example, if the retinal camera unit 2 has a case that is the similar to conventional retinal cameras, a joy stick, operation panel, etc. provided on this case may be included in the operation part 240B. Further, the display 240A may include various display devices such as a touch panel, etc. provided on the case of the retinal camera unit 2.

It should be noted that the display 240A and the operation part 240B do not need to be configured as separate devices. For example, like a touch panel, a device in which the display function and the operation function are integrated can be used. In such cases, the operation part 240B is configured to include this touch panel and a computer program. The content of operation via the operation part 240B is input to the controller 210 as an electric signal. Moreover, operations and inputs of information may be performed by using a graphical user interface (GUI) displayed on the display 240A and the operation part 240B.

OPERATIONS

Figure 6:
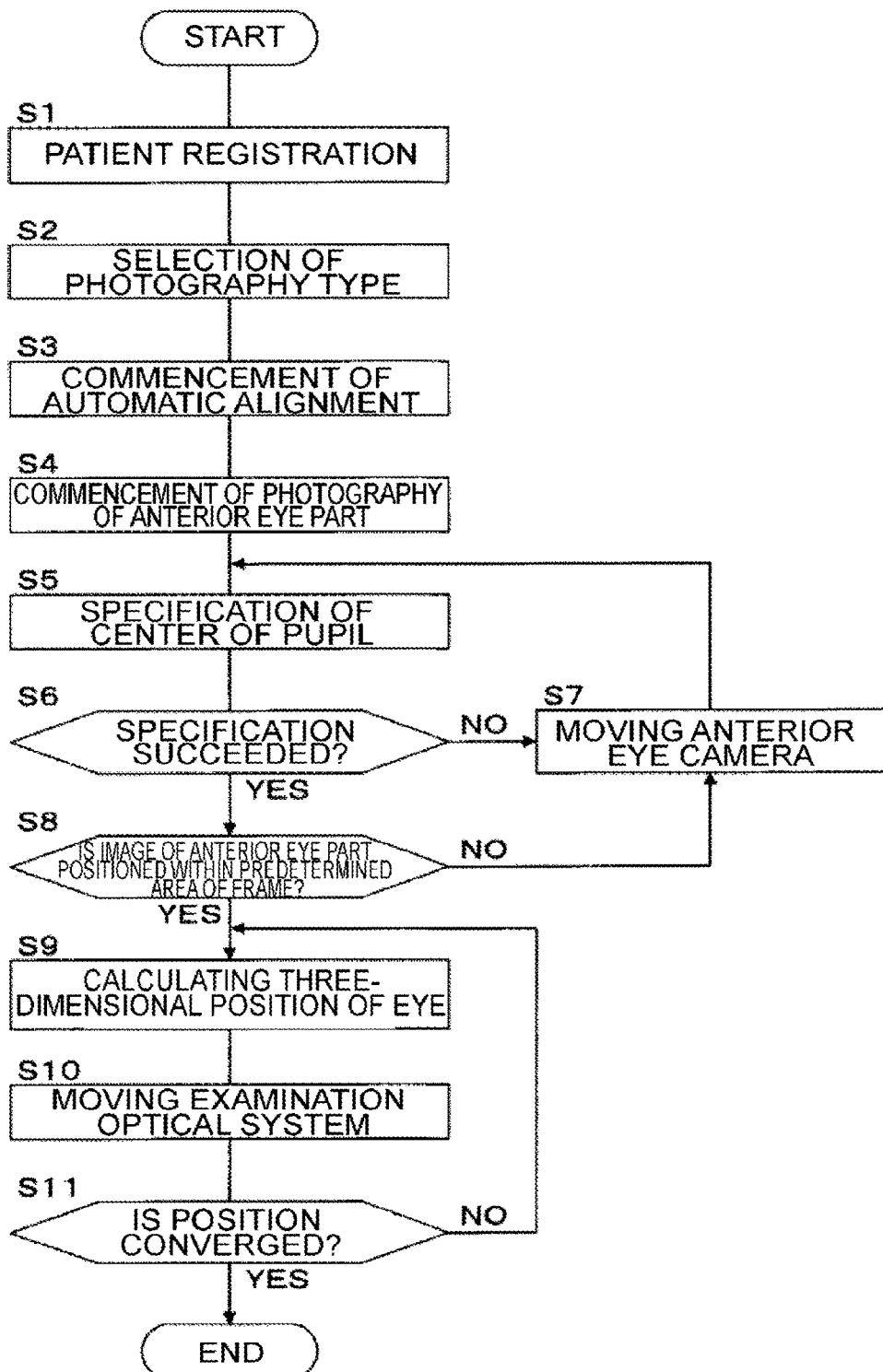
FIG. 6 is a flowchart illustrating an operational example of an ophthalmologic apparatus according to an embodiment.
Figure 7:
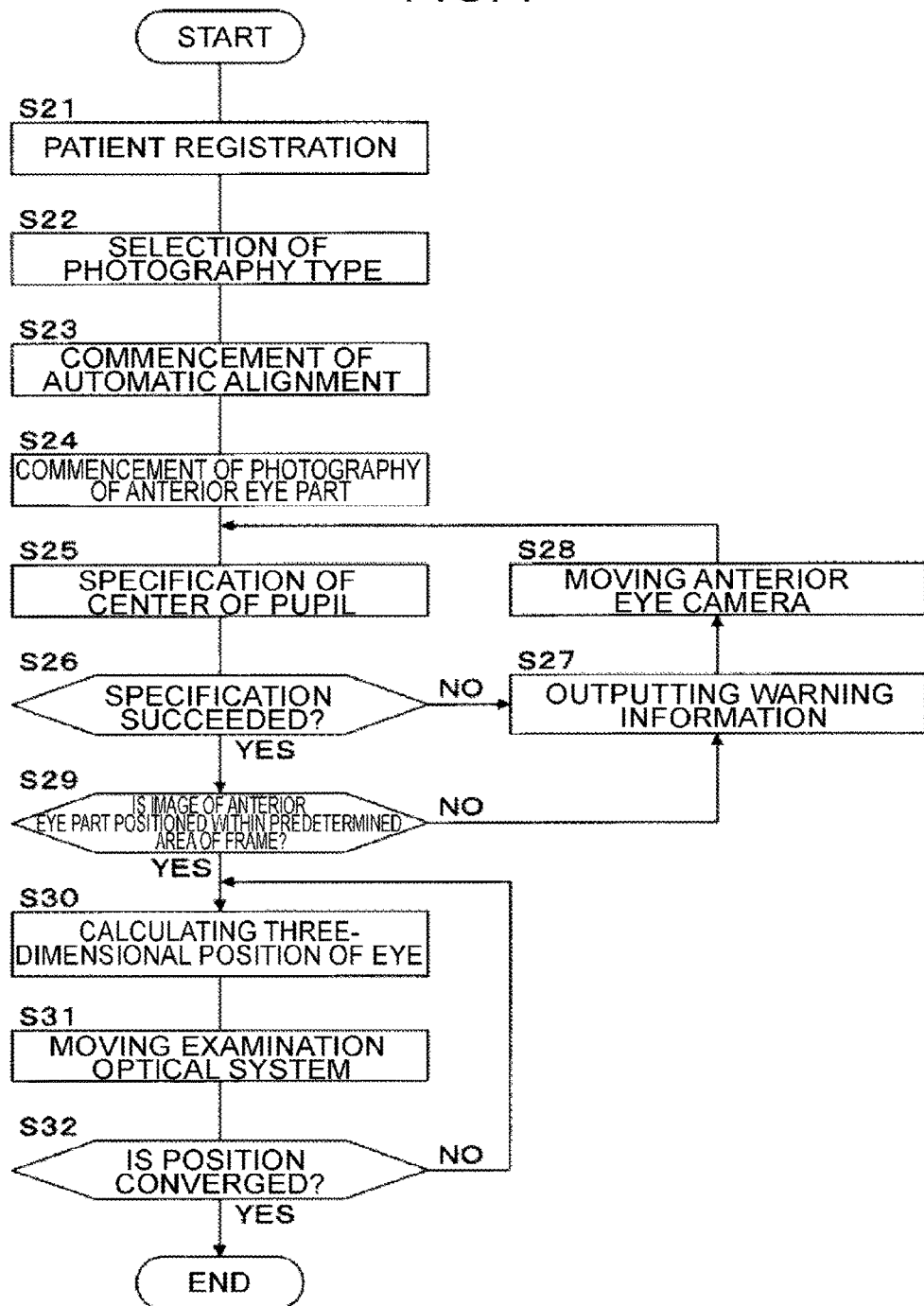
FIG. 7 is a flowchart illustrating an operational example of an ophthalmologic apparatus according to an embodiment.
Figure 8:
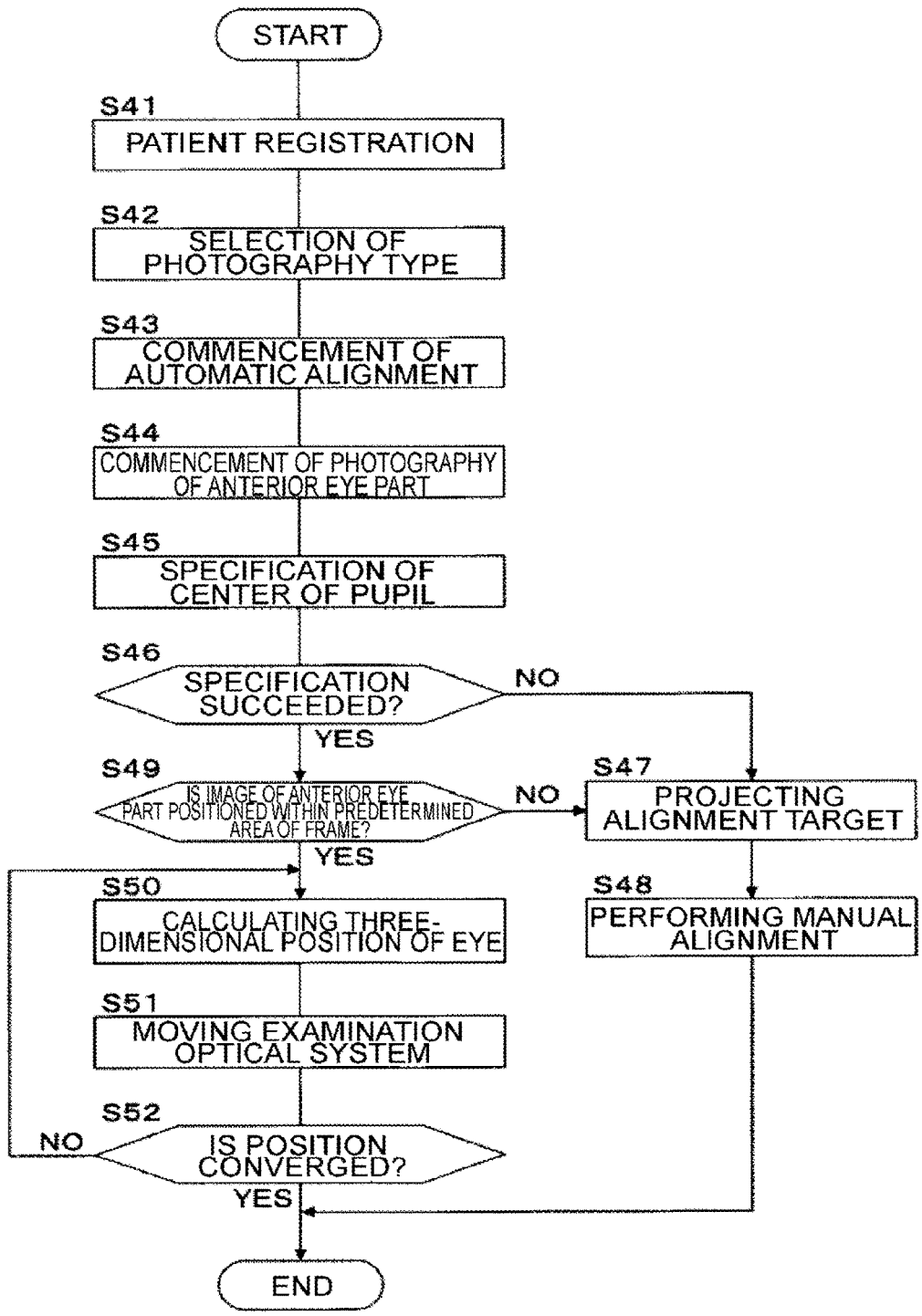
FIG. 8 is a flowchart illustrating an operational example of an ophthalmologic apparatus according to an embodiment.

Operations of the ophthalmologic apparatus 1 are described below. Examples of operations of the ophthalmologic apparatus 1 are illustrated in FIG. 6 to FIG. 8. It should be noted that any two or more of these operation examples may be combined.

Operation Example 1

A first operation example is described while referring to FIG. 6. The operation example 1 explains the fundamental flow of automatic alignment by the ophthalmologic apparatus 1 and the processes that are carried out in the event of failure in specifying the characteristic part of the anterior eye part Ea (here, the center of the pupil) or when the image of the anterior eye part Ea is not included in the predetermined area of a photograph image.

(S1: Patient Registration)

First, the user inputs patient information on a subject using the user interface 240. The patient information may be a patient ID, patient name, etc.

(S2: Selection of Photography Type)

Next, the user uses the user interface 240 to select and input the type of photography carried out with respect to the subject. The items of the photography type may include, for example, a photographing site (optic papilla, macula, or both, etc.), the photographed eye (left eye, right eye, both eyes), image photographing pattern (only a fundus image, only an OCT image, or both), OCT scanning pattern (line scan, cross scan, radial scan, circle scan, three-dimensional scan, etc.)

(S3: Commencement of Automatic Alignment)

Once the selection of the photography type is completed, an instruction for commencing automatic alignment is given. This commencement instruction may be automatically given by the controller 210 upon receiving the selection of the photography type shown in Step S2 or may be manually given by the user using the operation part 240B.

(S4: Commencement of Photography of Anterior Eye Part)

Once the instruction for commencing automatic alignment is given, the controller 210 causes the respective anterior eye cameras 300A and 300B to commence photographing of the anterior eye part Ea. This photographing is moving image photography of the anterior eye part Ea as the photography subject. The respective anterior eye cameras 300A and 300B carry out moving image photography at a predetermined frame rate. Here, the timings of photographing by the anterior eye cameras 300A and 300B may be synchronized by the controller 210. The respective anterior eye cameras 300A and 300B successively transmit the acquired frames to the controller 210 in real time. The controller 210 associates the frames obtained by both anterior eye cameras 300A and 300B in accordance with the photography timing. That is, the controller 210 associates the frames substantially simultaneously acquired by both anterior eye cameras 300A and 300B with each other. This association is carried out based on, for example, the abovementioned synchronous control or based on the input timings of the frames from the anterior eye cameras 300A and 300B. The controller 210 transmits the pair of the associated frames to the analyzer 231.

(S5: Specification of Center of Pupil)

The image correction part 2311 corrects the distortion of each frame transmitted from the controller 210 based on the aberration information 212a stored in the storage 212. This correcting process is carried out in the abovementioned manner. The pair of frames with the distortion thereof corrected is transmitted to the characteristic position specifying part 2312.

The characteristic position specifying part 2312 analyzes each frame transmitted from the image correction part 2311, thereby carrying out the process for specifying the characteristic position in the frame corresponding to the center of the pupil of the anterior eye part Ea.

(S6: Specification Succeeded?)

In the event of failure in specifying the characteristic position corresponding to the center of the pupil (S6: NO), the characteristic position specifying part 2312 transmits information indicating this result to the controller 210, and the process is transferred to Step S7. On the other hand, if specification of the center of the pupil has been successful (S6: YES), it shifts to Step S8.

(S7: Moving Anterior Eye Camera)

In the event of failure in specifying the characteristic position (S6: NO), the controller 210, in response to reception of the information from the characteristic position specifying part 2312, controls the camera moving part mentioned above to move the anterior eye cameras 300A and 300B in the direction away from the supporting part 440 and/or the direction outwards of the supporting part 440.

In the event of moving the anterior eye cameras 300A and 300B in the direction away from the supporting part 440, the distance between the anterior eye cameras 300A and 300B and the subject (the eye E) increases; thereby, it becomes possible to photograph a wider scope of the subject's face, increasing the possibility of the eye E being positioned in a range suitable for photographing by the anterior eye cameras 300A and 300B. Moreover, in the event of moving the anterior eye cameras 300A and 300B in the direction outwards of the supporting part 440, the anterior eye cameras 300A and 300B move in the direction of the subject's ear, increasing the possibility of the eye E being positioned in a range suitable for photographing by the anterior eye cameras 300A and 300B. Moreover, by combining the movement in these two directions, the possibility of the eye E being positioned in a range suitable for photographing is further enhanced.

In this operation example, it is regarded that the moving image photography of the anterior eye part Ea is continued even while moving or after moving the anterior eye cameras 300A and 300B. Instead, it is possible to stop the moving image photography upon moving the anterior eye cameras 300A and 300B and automatically or manually restart the moving image photography after the movement is completed.

After completion of movement of the anterior eye cameras 300A and 300B in Step S7, moving image photography by the anterior eye cameras 300A and 300B, specification of the center of the pupil (Step S5), and determination for successful specification (Step S6) are carried out again. It should be noted that a configuration is possible in which the process is transferred to manual alignment when this routine is repeated a predetermined number of times.

(S8: Is Image of Anterior Eye Part Positioned within Predetermined Area of Frame?)

Upon successful specification of the characteristic position corresponding to the center of the pupil (S6: YES), the image judging part 232 determines whether or not the image corresponding to the anterior eye part Ea is within a predetermined area of the frame. In this operation example, this determination process is carried out using the characteristic position specified in Step S6. Alternatively, when using other information to carry out the determination process, order of Steps S5 and S6 and Step S8 may be arbitrary.

In the event determination is made that the image of the anterior eye part Ea is not positioned within a predetermined area of the frame (S8: NO), the process is transferred to Step S7 and the abovementioned process is carried out. On the other hand, in the event determination is made that the image of the anterior eye part Ea is positioned within a predetermined area of the frame (S8: YES), the process is transferred to Step S9.

(S9: Calculating Three-Dimensional Position of Eye)

The three-dimensional position calculating part 2313 calculates the three-dimensional position of the center of the pupil of the eye E based on the positions of the anterior eye cameras 300A and 300B and the characteristic position specified by the characteristic position specifying part 2312 regarding the pair of frames. This process is carried out in the abovementioned manner.

(S10: Moving Examination Optical System)

Based on the three-dimensional position of the center of the pupil calculated in Step S9, the controller 210 controls the optical system driver 2A so as to match the optical axis of the examination optical system with the axis of the eye E, and such that the distance of the examination optical system with respect to the eye E becomes the preset working distance.

(S11: Is Position Converged?)

When the examination optical system is moved as shown in Step S10, the controller 210 determines whether or not the position of the examination optical system has converged. This determination process is carried out by, for example, using the alignment target. The observation condition of the alignment target changes depending on the alignment state.

Specifically, when the alignment is in a suitable state, two images of the alignment target are observed in substantially the same position, while the more the alignment state worsen, the more the two images are observed apart from each other. The controller 210 obtains the distance between these two images photographed by the CCD image sensor 35, and determines whether or not this distance is within a preset threshold or less. When determination is made that the distance is equal to the preset threshold or less (S11: YES), it is determined that the position of the examination optical system is converged, completing the process. Whereas, when determination is made that this distance exceeds the preset threshold (S11: NO), it is judged that the position of the examination optical system is not converged, returning to Step 9. The processes from Step 9 to Step 11 are repeated until, for example, determination "NO" is obtained in Step 11 a specific number of times. In the event the determination "NO" in Step 11 is repeated the specific number of times, the controller 210 outputs, for example, a specific warning information. Moreover, in response to the fact in which determination "NO" is repeated the specific number of times, the controller 210 may execute control of transferring to an operation mode for carrying out manual alignment or an operation mode for automatic alignment using the alignment target. It should be noted that such position convergence determination process is not limited to this, and any method is possible as long as the process is capable of judging whether or not the position of the examination optical system is appropriately converged.

This concludes the explanation of the automatic alignment according to this operation example. It should be noted that tracking of examination optical system may be executed by repeatedly carrying out Step S4 (moving image photography) to Step S11 (judgment of position convergence). Further, the explanation of Step S11 describes that the process returns to Step S9 when the position of the examination optical system is not converged (S11: NO); however, a configuration may be applied in which the process returns to Step S5 (specification of the center of the pupil). Specifically, frames are successively acquired at predetermined time interval after photography of the anterior eye is started in Step S4, and the processes from Step S5 are executed for the respective frames (or for each of frames obtained by thinning down). When judgment of position convergence in Step S11 is executed again, the processes of Step S5 to Step S10 are executed for newly acquired frames and upon receiving result thereof, judgment of position convergence is executed again.

Operation Example 2

A second operation example is described while referring to FIG. 7. In the operation example 2, warning information is output in the event of failure in specifying the characteristic part of the anterior eye part Ea (here, the center of the pupil) or when the image of the anterior eye part Ea is not included in the predetermined area of a photograph image.
(S21 to S25: Patient Registration to Specification of Pupil Center)

Step S21 to Step S25 are carried out in same manner as Step S1 to Step S5 in the operation example 1.
(S26: Specification Succeeded?)

In the event of failure in specifying the characteristic position corresponding to the center of the pupil (S26: NO), the characteristic position specifying part 2312 transmits information indicating this result to the controller 210, and the process is transferred to Step S27. On the other hand, if specification of the center of the pupil has been successful (S26: YES), it shifts to Step S29.
(S27: Outputting Warning Information)

In the event of failure in specifying the characteristic position (S26: NO), the controller 210 outputs the above-mentioned warning information in response to receiving the information from the characteristic position specifying part 2312.
(S28: Moving Anterior Eye Camera)

The user recognizes the warning information and moves the anterior eye cameras 300A and 300B by using the operation part 240B. Here, the controller 210 may display images photographed by the anterior eye cameras 300A and 300B on the display 240A. The user may carry out an operation for moving the anterior eye cameras 300A and 300B while referring to the displayed images.

After completion of operation for moving the anterior eye cameras 300A and 300B in Step S28, moving image photography by the anterior eye cameras 300A and 300B, specification of the center of the pupil (Step S25), and determination for successful specification (Step S26) are carried out again. It should be noted that a configuration is possible in which the process is transferred to manual alignment when this routine is repeated a predetermined number of times.
(S29: Is Image of Anterior Eye Part Positioned within Predetermined Area of Frame?)

Upon successful specification of the characteristic position corresponding to the center of the pupil (S26: YES), the image judging part 232 determines whether or not the image corresponding to the anterior eye part Ea is within a predetermined area of the frame in the same way as the operation example 1.

In the event determination is made that the image of the anterior eye part Ea is not positioned within a predetermined area of the frame (S29: NO), the process is transferred to Step S27 to output warning information, and further, transferred to Step S28 to carry out operation for moving the anterior eye cameras 300A and 300B. On the other hand, in the event determination is made that the image of the anterior eye part Ea is positioned within a predetermined area of the frame (S29: YES), the process is transferred to Step S30.
(S30: Calculating Three-Dimensional Position of Eye)

Similar to the operation example 1, the three-dimensional position calculating part 2313 calculates the three-dimensional position of the center of the pupil of the eye E based on the positions of the anterior eye cameras 300A and 300B and the characteristic position specified by the characteristic position specifying part 2312 regarding the pair of frames.
(S31: Moving Examination Optical System)

Based on the three-dimensional position of the center of the pupil calculated in Step S30, the controller 210 controls the optical system driver 2A so as to match the optical axis of the examination optical system with the axis of the eye E, and such that the distance of the examination optical system with respect to the eye E becomes the preset working distance. This process is executed as in Step S10 of the operation example 1.
(S32: Is Position Converged?)

When the examination optical system is moved as shown in Step S31, the controller 210 executes process of judging position convergence as in the Step S11 of the operation example 1. When determination is made that the position of the examination optical system is converged (S32: YES), the process is completed. On the other hand, when determination is made that the position of the examination optical system is not converged (S32: NO), the process returns to Step S30. Repetition of processes of Step S30 to Step S32 and warning may be similar to those in the operation example 1. This completes the explanation of this operation example.

Operation Example 3

A third operation example is described while referring to FIG. 8. In the operation example 3, the process is transferred to manual alignment in the event of failure in specifying the characteristic part of the anterior eye part Ea (here, the center of the pupil) or when the image of the anterior eye part Ea is not included in the predetermined area of a photograph image.
(S41 to S45: Patient Registration to Specification of Pupil Center)

Step S41 to Step S45 are carried out in same manner as Step S1 to Step S5 in the operation example 1.
(S46: Specification Succeeded?)

In the event of failure in specifying the characteristic position corresponding to the center of the pupil (S46: NO), the characteristic position specifying part 2312 transmits information indicating this result to the controller 210, and the process is transferred to Step S47. On the other hand, if specification of the center of the pupil has been successful (S46: YES), it shifts to Step S49.
(S47: Projecting Alignment Target)

In the event of failure in specifying the characteristic position (S46: NO), the controller 210 controls the alignment optical system 50 to project the alignment target onto the eye E in response to receiving the information from the characteristic position specifying part 2312. Further, the controller 210 controls the retinal camera unit 2 and the display 240A to display an observation image (moving image) of the anterior eye part Ea onto which the alignment target is projected.
(S48: Performing Manual Alignment)

The user performs manual alignment by using the operation part 240B while referring to the observation image displayed. The process in this case is completed here. It may be configured to transfer to manual alignment when the routine of moving image photography by the anterior eye cameras 300A and 300B, specification of the center of the pupil (Step S45), and determination for successful specification (Step S46) is repeated a predetermined number of times.
(S49: Is Image of Anterior Eye Part Positioned within Predetermined Area of Frame?)

Upon successful specification of the characteristic position corresponding to the center of the pupil (S46: YES), the image judging part 232 determines whether or not the image corresponding to the anterior eye part Ea is within a predetermined area of the frame in the same way as the operation example 1.

In the event determination is made that the image of the anterior eye part Ea is not positioned within a predetermined area of the frame (S49: NO), the process is transferred to Step S47 to project the alignment target onto the eye E, and further, transferred to Step S48 to carry out manual alignment. On the other hand, in the event determination is made that the image of the anterior eye part Ea is positioned within a predetermined area of the frame (S49: YES), the process is transferred to Step S50.
(S50: Calculating Three-Dimensional Position of Eye)

Similar to the operation example 1, the three-dimensional position calculating part 2313 calculates the three-dimensional position of the center of the pupil of the eye E based on the positions of the anterior eye cameras 300A and 300B and the characteristic position specified by the characteristic position specifying part 2312 regarding the pair of frames.
(S51: Moving Examination Optical System)

Based on the three-dimensional position of the center of the pupil calculated in Step S50, the controller 210 controls the optical system driver 2A so as to match the optical axis of the examination optical system with the axis of the eye E, and such that the distance of the examination optical system with respect to the eye E becomes the preset working distance. This process is executed as in Step S10 of the operation example 1.

It should be noted that after manual alignment of Step S48 is executed, information indicating the characteristic part of the anterior eye part Ea specified based on the result of this manual alignment may be displayed. This process is carried out by, for example, the following way: the characteristic position specifying part 2312 specified the image position in (frames of) the observation image that corresponds to the characteristic part; and the controller 210 displays information indicating the specified image position over the observation image.
(S52: Is Position Converged?)

When the examination optical system is moved as shown in Step S51, the controller 210 executes process of judging position convergence as in the Step S11 of the operation example 1. When determination is made that the position of the examination optical system is converged (S52: YES), the process is completed. On the other hand, when determination is made that the position of the examination optical system is not converged (S52: NO), the process returns to Step S50. Repetition of processes of Step S50 to Step S52 and warning may be similar to those in the operation example 1. This completes the explanation of this operation example.

Operation Example 4

A fourth operation example may be applied in combination with arbitrary operation modes of this embodiment including the first to third operation examples.

The fourth operation example is executed by using the image synthesis part 233. Specifically, the controller 210 controls the image synthesis part 233 to form a synthetic image of two photograph images that are substantially simultaneously obtained by the two anterior eye cameras 300A and 300B. This synthetic image is a stereoscopic image or a viewpoint-converted image as described above, for example. It should be noted that timing for executing the process of this operation example may be any timing after two photograph images are obtained.
[Actions and Effects]

Actions and Effects of the ophthalmologic apparatus 1 are explained.

The ophthalmologic apparatus 1 includes: a retinal camera optical system and an OCT optical system (examination optical system); the supporting part 440; the optical system driver 2A (driver, first driver); two or more anterior eye cameras 300A and 300B (imaging parts); the analyzer 231; and the controller 210.

The examination optical system is an optical system for examining the eye E and is used for acquiring images of the eye in this embodiment.

The optical system driver 2A moves the examination optical system three-dimensionally. Thereby, the examination optical system and the supporting part 440 are moved relatively and three-dimensionally.

The anterior eye cameras 300A and 300B substantially simultaneously photograph the anterior eye part Ea of the eye E from different directions. It should be noted that although two imaging parts are provided in this embodiment, the number thereof may be arbitrary (equal to or more than two). Here, taking purpose of use of images acquired by imaging parts into consideration, two imaging parts are enough. However, a configuration may be applied in which three or more imaging parts having different imaging areas are used, preferable images (for example, those in which the anterior eye parts Ea is preferably depicted) are selected from the three or more images acquired substantially simultaneously, and the selected images are provided for processes in latter steps.

The analyzer 231 obtains three-dimensional position of the eye E by analyzing two photograph images acquired by the two anterior eye cameras 300A and 300B substantially simultaneously.

The controller 210 controls the optical system driver 2A based on the three-dimensional position of the eye E obtained by the analyzer 231 to relatively move the examination optical system and the supporting part 440. More specifically, the controller 210 of this embodiment controls the optical system driver 2A based on the three-dimensional position of the eye E obtained by the analyzer 231 so as to align an optical axis of the examination optical system with an axis of the eye E and adjust a distance between the eye E and the examination optical system to a preset working distance. Here, the axis of the eye E may be an arbitrary axis defined in directions from cornea side of the eye E to retina side, and examples of which include an eye axis and visual axis (optic axis). Further, the axis of the eye E may include an error within a permissible range (measurement error, instrumental error, etc.). For example, although this embodiment analyzes images to obtain the characteristic part (such as pupil center, corneal apex) of the anterior part Ea, the positions of the pupil center and corneal apex do not generally coincide with each other when the eye is seen from the front side. The axis of the eye E may include an error within a range determined by taking such situations into consideration. It should be noted that since examinations using the examination optical system (such as fundus photography, OCT measurement) are performed after alignment and tracking in this embodiment, an error of the axis of the eye E is permissible within a range to the extent that bad influence is given to latter examinations.

The analyzer 231 may include the characteristic position specifying part 2312 and the three-dimensional position calculating part 2313. The characteristic position specifying part 2312 analyzes each of the two photograph images acquired by the two anterior eye cameras 300A and 300B substantially simultaneously to specify a characteristic position in this photograph image that corresponds to a predetermined characteristic part of the anterior eye part Ea. This characteristic part is a pupil center or corneal apex, for example. The three-dimensional position calculating part 2313 obtains a three-dimensional position of the characteristic part based on positions of the two anterior eye cameras 300A and 300B and the characteristic positions in the two photograph images. This three-dimensional position of the characteristic part is used as the three-dimensional position of the eye E.

Further, the optical system position obtaining part 213 that obtains a current position of the examination optical system may be provided in the controller 210. In this case, the controller 210 is configured control the optical system driver 2A to move the examination optical system based on the current position obtained by the optical system position obtaining part 213 and the three-dimensional position of the eye E obtained by the analyzer 231.

According to the ophthalmologic apparatus 1 thus configured, positional relationship between the eye E and the examination optical system based on two or more photograph images acquired substantially simultaneously, which is different from conventional apparatuses in which position matching in the xy-direction (direction perpendicular to the optical axis) and position matching in the z-direction (direction along the optical axis) are performed with different methods. Therefore, it is possible to carry out three-dimensional position matching between the eye E and the optical system of the ophthalmologic apparatus 1 with high accuracy.

The ophthalmologic apparatus 1 may include the moving-image acquiring optical system, the alignment optical system 50 (projecting optical system), the display 240A and the operation part 240B. The moving-image acquiring optical system acquires moving images of the anterior eye part Ea of the eye E, and a part of the optical path of the moving-image acquiring optical system is shared with the examination optical system. In this embodiment, portion of the retinal camera optical system for acquiring observation images is used as the moving-image acquiring optical system. Further, this moving-image acquiring optical system and the OCT optical system share parts of their optical paths (namely, between the objective lens 22 and the dichroic mirror 46). The alignment optical system 50 projects a target (the alignment target) for executing position matching of the examination optical system with the eye E onto the eye E. The controller 210 switches operation mode to manual alignment mode when the characteristic position or the eye E has not been specified by the characteristic position specifying part 2312. Specifically, when the characteristic position or the anterior eye part Ea has not been specified, the controller 210 executes the following actions: (1) controlling the alignment optical system 50 to project the alignment target onto the eye E; (2) controlling the moving-image acquiring optical system to acquire the moving image of the anterior eye part Ea onto which the alignment target is being projected; (3) controlling the display 240A to display the moving image of the anterior eye part Ea acquired by the moving-image acquiring optical system; and (4) controlling the optical system driver 2A to move the examination optical system in accordance with an operation carried out by using the operation part 240B while referring to the displayed moving image. Such a switching of operation modes makes it possible to smoothly transfer manual alignment In a case in which automatic alignment based on two or more photograph images has not been successful. Therefore, examination time may be shortened and burdens on patients and examiner may be reduced.

The following configuration may be applied: after the manual alignment based on the above switching of operation modes, the characteristic position specifying part 2312 specifies an image position in the moving image that corresponds to the above characteristic part; and the controller 210 displays information indicating the specified image position over the moving image. According to this configuration, it is possible to recognize, in real time, the characteristic position specified based on the result of the manual alignment by referring to the moving image. It should be noted that in this process, the characteristic position specifying part 2312 may specify the above image position in respective frames successively acquired after manual alignment, and the controller 210 may display information indicating the image position over the respective frames. Form this, a moving image is obtained in which the position of this image position in the frames varies in accordance with the movement of the eye E.

The following configuration may be applied for executing tracking similar to the abovementioned automatic alignment. To achieve this: the two or more imaging parts acquire moving images of the anterior eye part Ea of the eye E from different directions in parallel; the analyzer 231 successively analyzes two or more frames acquired substantially simultaneously in this moving image acquisition to obtain the three-dimensional positions of the eye successively; and the controller 210 successively controls the optical system driver 2A based on the three-dimensional positions successively obtained by the analyzer 231 to make the position of the examination optical system follow movement of the eye E. such a configuration makes it possible to realize tracking with high accuracy.

Processing executed by the analyzer 231 for obtaining the three-dimensional position of the eye E may be carried out as follows. In this configuration, the ophthalmologic apparatus 1 includes storage 212 (as the second storage) in which the aberration information 212a of the respective imaging parts is stored in advance. The aberration information 212a is information relating distortion aberration occurring in photograph images due to the optical systems of the imaging parts. The aberration information 212a may be generated by photographing reference points using a concerned imaging part while changing the position of this imaging part relative to the reference points and by analyzing multiple photograph images thus acquired. The analyzer 231 includes the image correction part 2311 that corrects distortion of the respective photograph images based on the aberration information corresponding to the concerned imaging part. Further, the analyzer 231 obtains the three-dimensional position of the eye E based on the two or more photograph images corrected by the image correction part 2311. According to such a configuration, distortion aberration due to the optical systems of the respective imaging parts may be taken into consideration, thereby making it possible to carry out alignment and tracking with higher accuracy.

In a case in which the eye E is not located at an appropriate position for examination, the imaging parts may be moved to suitable locations. To achieve this, the ophthalmologic apparatus 1 may be provided with the photography moving part, the supporting part 440 and the image judging part 232 (judging part). The photography moving part moves at least one or the two or more imaging parts. The supporting part 440 supports the face of the subject. The image judging part 232 analyzes a photograph image acquired by at least one of the two or more imaging parts to judge whether or not an image of the anterior eye part Ea is included in a preset region in this photograph image. When the image of the anterior eye part Ea is not included in the preset region, the controller 210 controls the photography moving part to move at least one of the two or more imaging parts in a direction away from the supporting part 440 and/or a direction away from the optical axis of the examination optical system. Then, the image judging part 232 executes the above judgment again. According to such a configuration, if the eye E is located at an position inappropriate for examination, it is possible to move the imaging part(s) in a direction that is thought to be preferable for photography of the eye E and carry out the judgment process again. It should be noted that examples of such a process include a method of executing the judgment process stepwise while moving the imaging part(s) by preset distance in stages, a method of executing the judgment process in real time while continuously moving the imaging part(s) at preset speed. Further, when it is determined in the above judgment process that the image of the anterior eye part Ea is located within the preset region in the photograph image, the controller 210 transfers to control for leaving the routine for moving the imaging parts and control for executing latter processes.

The ophthalmologic apparatus 1 may include the image synthesis part 233 that forms a synthetic image of the two or more photograph images acquired substantially simultaneously by the two or more imaging parts. If this is the case, the controller 210 may display the synthetic image formed by the image synthesis part 233 on a display 240A. The synthetic image is a stereoscopic image or a viewpoint-converted image as described above, for example. Such a configuration realizes various observation modes (such as stereoscopic image observation, observation from different viewpoints, etc.) of the eye E.

Second Embodiment

The first embodiment described above realizes relative movement between the examination optical system and the supporting part 440 by means of moving the examination optical system. In a second embodiment, a case is described in which the relative movement is realized by applying a configuration capable of moving the supporting part 440. Hereinafter, the same symbols are used for similar elements to those in the first embodiment. Further, an ophthalmologic apparatus of the present embodiment is indicated by the symbol 1000.

<Configuration>

Figure 9:
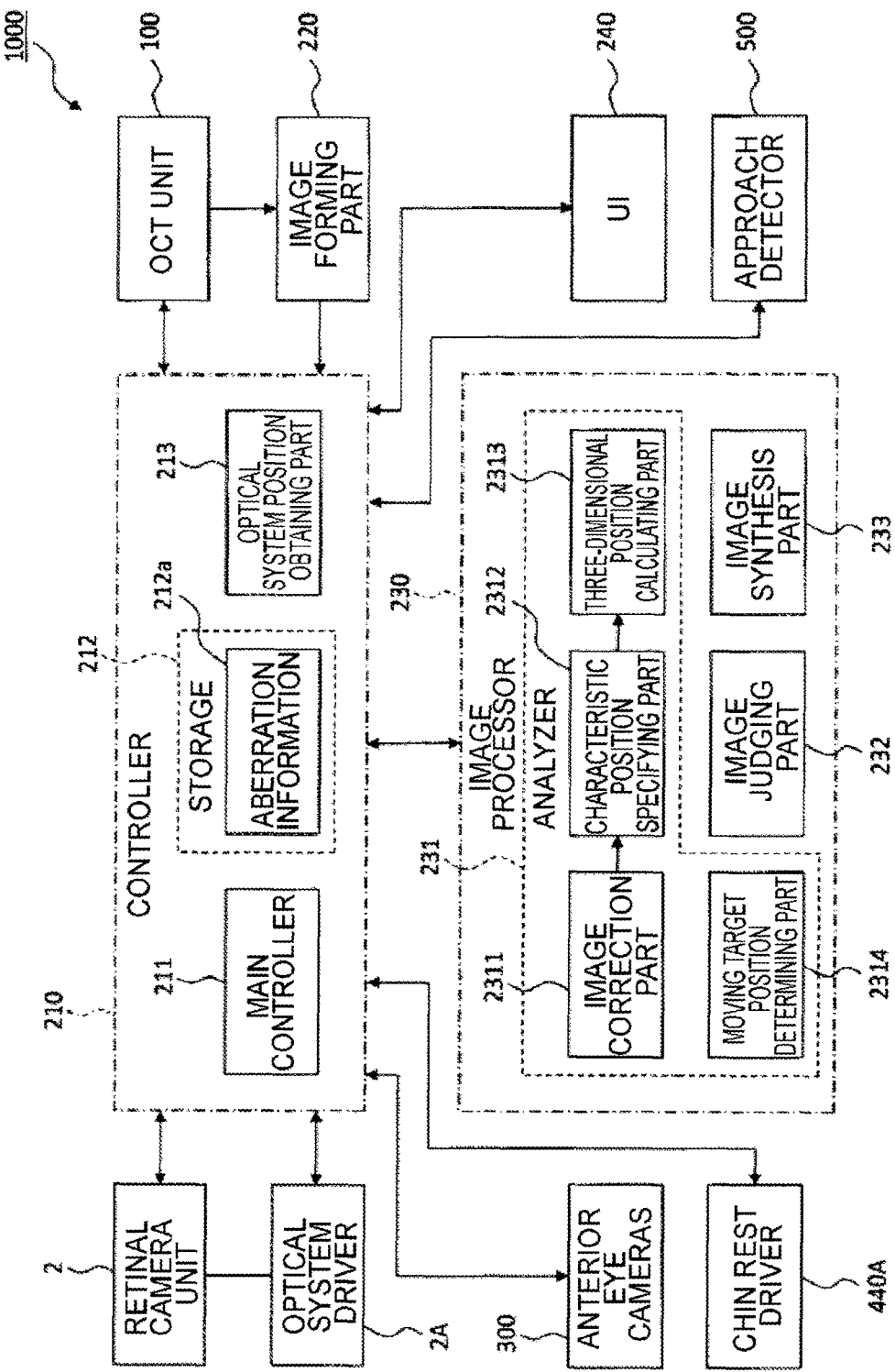
FIG. 9 is a schematic block diagram illustrating an example of a configuration of an ophthalmologic apparatus according to an embodiment.

The ophthalmologic apparatus 1000 includes almost the same hardware configuration as the ophthalmologic apparatus 1 of the first embodiment (refer to FIG. 1 and FIG. 2), for example. FIG. 9 illustrates a configuration example of the control system of the ophthalmologic apparatus 1000. Differences from the control system of the first embodiment illustrated in FIG. 3 are the following: a moving target position determining part 2314 is provided in the analyzer 231; and a chin rest driver 440A and an approach detector 500 are provided. It should be noted that, although illustration is omitted, the display 240A and the operation part 240B are provided in the user interface 240 as in the first embodiment. Further, description regarding elements common to the first embodiment is omitted; however, the ophthalmologic apparatus 1000 is capable of executing processes similar to the first embodiment by means of these common elements. Hereinafter, items different from the first embodiment are selectively described.

(Chin Rest Driver)

The chin rest driver 440A moves the supporting part 440 upon receiving control from the main controller 211. The chin rest driver 440A moves the supporting part 440 at lease in the vertical direction. That is, the chin rest driver 440A may be configured to move the supporting part 440 in the vertical direction only, or may be configured to move the supporting part 440 in the left/right direction and/or the front/rear direction in addition to the vertical direction. The chin rest driver 440A is an example of a "second driver".

It should be noted that the second driver in the present embodiment functions to move multiple members that support the face of the subject (chin rest, forehead rest, etc.) integrally; however, it may be configured to move the respective members separately. For example, it may be configured that a driving mechanism for moving the chin rest and a driving mechanism for moving the forehead rest are provided separately.

(Moving Target Position Determining Part)

The moving target position determining part 2314 determines a moving target position of the supporting part 440 based on two photograph images substantially simultaneously acquired by the anterior eye cameras 300A and 300B and positions of the anterior eye cameras 300A and 300B. The moving target position means a destination of the supporting part 400 in a latter movement process. Further, the moving target position means indicates a location in a movable direction of the supporting part 440 by the chin rest driver 440A. For example, in a case in which the supporting part 440 may be moved in the vertical direction, the moving target position indicates a location in the vertical direction (that is, a height position).

Examples of processes executed by the moving target position determining part 2314 are explained. On a presupposition, the ophthalmologic apparatus 1000 executes substantially simultaneous photography using the anterior eye cameras 300A and 300B to acquire two images from different viewpoints. The moving target position determining part 2314 applies known image processes (such as pattern matching, threshold process, etc.) to the two images to specify an image region corresponding to a predetermined site that is depicted in both two photograph images. The site is a part of the subject (an eye etc.), for example.

Further, the moving target position determining part 2314 obtains a three-dimensional position corresponding to the specified image region based on the parallax of the two photograph images acquired from locations of the anterior eye cameras 300A and 300B. This process may be carried out in a way similar to the process of obtaining the three-dimensional position of the eye E explained in the first embodiment, for example (refer to FIG. 5A and FIG. 5B).

It should be noted that the moving target position determining part 2314 may be configured to determine the moving target position based on images acquired by photographing the anterior eye part of the eye E, as explained in an operation example stated below. Further, since the position of the examination optical system and the position of the supporter 440 are relative, the moving target position determining part 2314 may determine the moving target position of the examination optical system (retinal camera unit 2).

(Approach Detector)

The approach detector 500 detects a state in which the subject approaches the supporting part 400. The approach detector 500 is configured to include a proximity sensor. The proximity sensor is also called a proximity switch and is a device that converts movement information and/or existence information of a detection object to electrical signals. Examples of detection methods applied to the proximity sensor include infrared light method, electrostatic capacity method, ultrasound method, etc. Further, an illuminance sensor for detecting brightness may be used as a proximity sensor.

An example is described in which approach of the subject is detected without the abovementioned sensors. Firstly, at least one of the anterior eye cameras 300A and 300B starts moving image acquisition. As the subject is approaching the supporting part 440, (the face of) the subject is coming into frames of the moving image. The image processor 230 analyzes the respective frames of the moving image to detect the event that the subject has come into the frames. Further, the image processor 230 analyzes the successively input frames to obtain time-series change in depiction size of (a predetermined site) of the face of the subject. Then, the image processor 230 judges that the subject is in the proximity of the supporting part 440 when the depiction size has become equal to or larger than a preset value. It should be noted that a parameter indicating the depiction size may be calculated on the bases of the size of frames and/or the size of depicted objects (the supporting part 400 etc.). When this example is applied, at least one of the anterior eye cameras 300A and 300B and the image processor 230 function as the approach detector 500.

OPERATIONS

Figure 10:
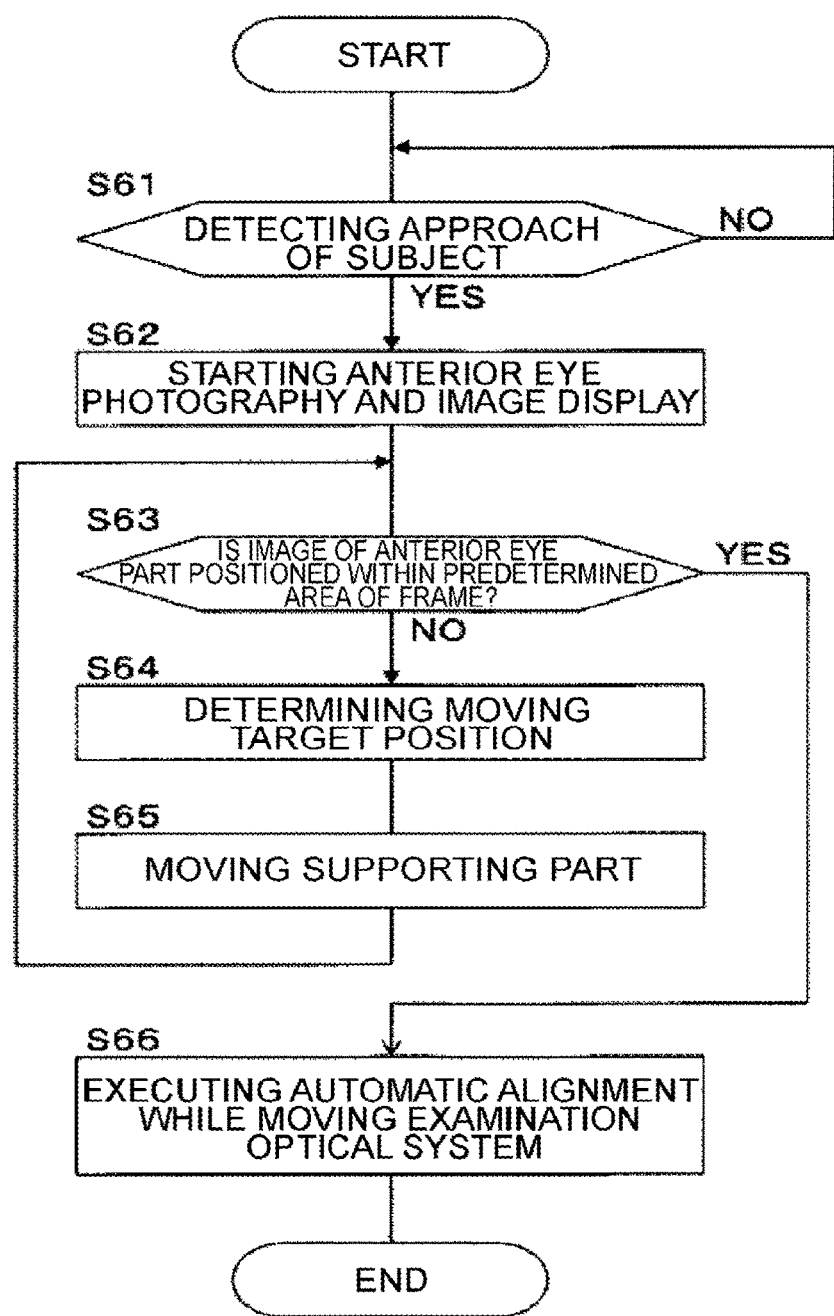
FIG. 10 is a flowchart illustrating an operational example of an ophthalmologic apparatus according to an embodiment.
Figure 11:
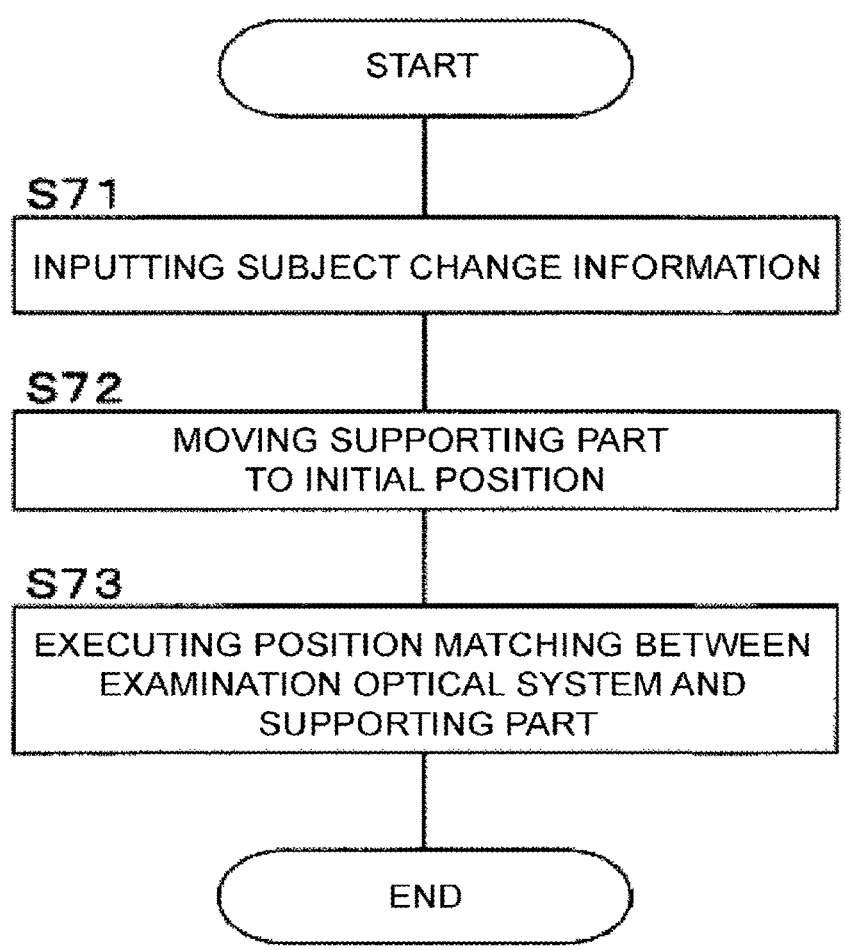
FIG. 11 is a flowchart illustrating an operational example of an ophthalmologic apparatus according to an embodiment.
Figure 12:
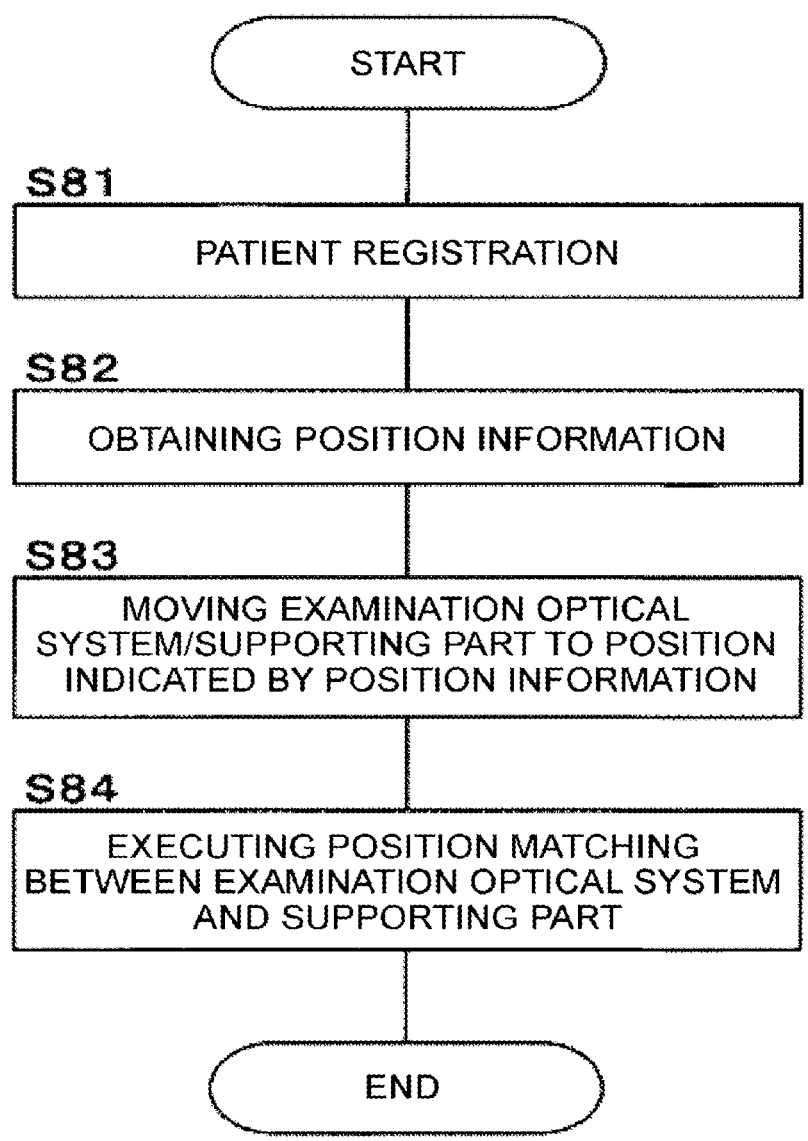
FIG. 12 is a flowchart illustrating an operational example of an ophthalmologic apparatus according to an embodiment.

Operations of the ophthalmologic apparatus 1000 are described below. Examples of operations of the ophthalmologic apparatus 1000 are illustrated in FIG. 10 to FIG. 12. It should be noted that any two or more of these operation examples may be combined. Further, any one of operation examples and any one of the operation examples described in the first embodiment may be combined.

Operation Example 1

A first operation example is described while referring to FIG. 10. It should be noted that the Step S1 (patient registration) and Step S2 (Selection of photography type) shown in FIG. 6 of the first embodiment may be executed at any timing before or during the processes illustrated in FIG. 10.

(S61: Detecting Approach of Subject)

Firstly, the main controller 211 starts the operation of the approach detector 500. Operation of the approach detector 500 continues at least until approach of the subject with respect to the supporting part 440 is detected (S61: NO).

(S62: Starting Anterior Eye Photography and Image Display)

When the approach detector 500 detects the approach of the subject with respect to the supporting part 440 (S61: YES), the main controller 211 controls the anterior eye cameras 300A and 300B to start imaging of the anterior eye part of the eye E. Further, the main controller 211 displays images acquired by one or both of the anterior eye cameras 300A and 300B in this anterior eye photography on the display 240A in real time. In the case of displaying both images, a displayed image may be a synthetic image (such as a stereoscopic image, a viewpoint-converted image, etc.) described above. Further, a process mode of this step is moving image acquisition and movie display.

(S63: Is Image of Anterior Eye Part Positioned within Predetermined Area of Frame?)

The analyzer 231 and the image judging part 232 analyze the images acquired in Step S62 to determine whether or not an image of the anterior eye part is depicted within a predetermined area of the frame. This process may be executed as in Step S6 to Step S8 of FIG. 6 of the first embodiment. Further, this process may be executed to the images, one after another, acquired in time series in the anterior eye photography started in Step S62.

When it is judged that the image of the anterior eye part is located within the predetermined area (S63: YES), processing is transferred to automatic alignment (moving examination optical system) of Step S66. On the other hand, when it is judged that the image of the anterior eye part is not located within the predetermined area (S63: NO), processing is transferred to Step S64 and Step S65 (moving supporting part 440).

(S64: Determining Moving Target Position)

When it is judged that the image of the anterior eye part is not located within the predetermined area (S63: NO), the moving target position determining part 2314 determines a moving target position of the supporting part 440 based on two photograph images substantially simultaneously acquired from the anterior eye photography of Step S62 and positions of the anterior eye cameras 300A and 300B.

(S65: Moving Supporting Part)

The main controller 211 controls the chin rest driver 440A so as to move the supporting part 440 to the moving target position determined in Step S64. Once movement of the supporting part 440 is completed, processing is returned to the judgment process of Step S63. More specifically, Step S63 to Step S65 are repeated until the judgment result "YES (the image of the anterior eye part is located within the predetermined area)" is obtained in Step S63.

For example, if the number of occurrence is reached to a preset number in this repetition or if the repetition is continued for a preset period of time, it is possible to stop the repetition and execute notification. This notification is, for example, a process of outputting information for inviting the user to manual position matching of the supporting part 440.

(S66: Executing Automatic Alignment while Moving Examination Optical System)

If judgment result "NO" is obtained in Step S63, the main controller 211 executes automatic alignment indicated in FIG. 6 (in particular, Step S9 to Step S11) of the first embodiment, for example. Consequently, the relative position between the eye E and the examination optical system is led to a positional relationship in which examination is executable.

Operation Example 2

A second operation example is described while referring to FIG. 11. Processes in this operation example are carried out in response to changes of subjects.

(S71: Inputting Subject Change Information)

Firstly, information indicating change of subjects (subject change information) is input to the main controller 211. This information input is carried out at a timing of ending an examination of one subject or at a timing of starting an examination of a new subject. Examples of the former include a timing of manual operation for ending an examination of one subject and a timing of executing a process of storing information acquired by an examination of one subject. Examples of the latter include a timing of manual operation for starting an examination of a new subject and a timing of the patient registration indicated in Step S1 of FIG. 6 of the first embodiment. Information indicating such an operation or processing corresponds to the subject change information. It should be noted that the subject change information indicating the fact that a predetermined operation has been carried out is input from the operation part 240B to the main controller 211. Further, since the main controller 211 realizes execution of a predetermined processing, it is considered that the subject change information in this case is input from the main controller 211 to itself.

(S72: Moving Supporting Part to Initial Position)

Upon receiving input of the subject change information, the main controller 211 controls the chin rest driver 440A to move the supporting part 440 to a preset initial position. This initial position is set in advance. For example, the initial position may be a height position calculated based on a standard value of information obtained by measuring a body (height, sitting height of body, etc.). Further, in the case in which height of a chair on which subjects sit is adjustable and height information of the chair is detectable, the initial position may be determined by taking the height of the chair into consideration. For example, the initial position may be determined based on the height of the chair and the above-mentioned standard value. Further, when patient registration has already carried out, the initial position may be determined based on the age, height, sitting height of a concerned subject. Further, when examinations are carried out to subject group with a specific age group (adults, children, etc.) or specific sex such as health examinations, multiple initial positions preliminary set according to the specific age group or sex may be applied selectively.

(S73: Executing Position Matching Between Examination Optical System and Supporting Part)

Once the supporting part 440 is moved to the initial position, position matching is executed for adjusting the relative position between the examination optical system and the supporting part 440. This position matching is an arbitrary operation example described in the first or second embodiment, for example.

Operation Example 3

A third operation example is described while referring to FIG. 12. This operation example is configured to move the examination optical system and the supporting part 440 to a position that was applied in an examination carried out to a concerned subject in the past.

On a presupposition, the ophthalmologic apparatus 1000 has a function to store position information indicating a position of the examination optical system and/or a position of the supporting part 440 applied in an examination, wherein the position information is associated with identification information (patient ID etc.) of a concerned subject. This process may include a process of associating a patient ID input in patient registration with position information in an actual examination, and storing them. As a specific example, medical records of the respective patients may be provided with regions for recording position information. Patient ID's and position information are stored in a storage device (the storage 212) provided in the ophthalmologic apparatus 1000 and/or a storage device of an external apparatus (medical record system). In the former case, the storage 212 functions as a "first storage". In the latter case, a process of associating position information generated in the ophthalmologic apparatus 1000 with a patient ID and transmitting them after temporarily storing the position information in the storage 212, and a process of acquiring position information stored in the past from the external apparatus, associating this position information with a patient ID and at least temporarily storing them in the storage 212; therefore, it may be considered that the first storage includes at least the storage 212.

(S81: Patient Registration)

Firstly, patient registration is carried out. The patient registration may be executed, as in the first embodiment, by inputting patient information of the subject (including identification information of the subject) using the user interface 240.

(S82: Obtaining Position Information)

The main controller 211 obtains position information that is associated with the identification information input in Step S81. This process may be carried out by retrieving position information in the storage 212 (or storage in the external apparatus) using the input identification information as a retrieval query.

It should be noted that there may be a case in which position information associated with the input identification information is not obtained. In such a case, it may be configured to notify information indicating aimed position information has not been obtained or information inviting the user to perform a predetermined alternative process instead of processes described below. The alternative process may be manual position matching or any process described in the first or second embodiment.

(S83: Moving Examination Optical System/Supporting Part to Position Indicated by Position Information)

The main controller 211 controls the optical system driver 2A and/or the chin rest driver 440A so as to move the examination optical system and/or the supporting part 440 to a position indicated by the position information obtained in Step S82. In this process, if both positions of the examination optical system and the supporting part 440 are included in the position information, both or any one of these may be moved. Alternatively, if only one of positions of the examination optical system and the supporting part 440 is included in the position information, this one of these may be moved.

(S84: Executing Position Matching Between Examination Optical System and Supporting Part)

Once the examination optical system and/or the supporting part 440 are/is moved to the position indicated by the position information, position matching for adjusting relative position between the examination optical system and the supporting part 440. This position matching may be any operation example described in the first or second embodiment.

It should be noted that a reason why the position matching of Step S84 is executed is because the process of Step S83 is not enough to arrange the eye E and the examination optical system in preferable positional relationship in general. This is because position of the face abutting on the supporting part 440 is slightly different each time, and extremely precise position matching is needed for examinations of the eye E, for example.

Modified Example

Figure 13:
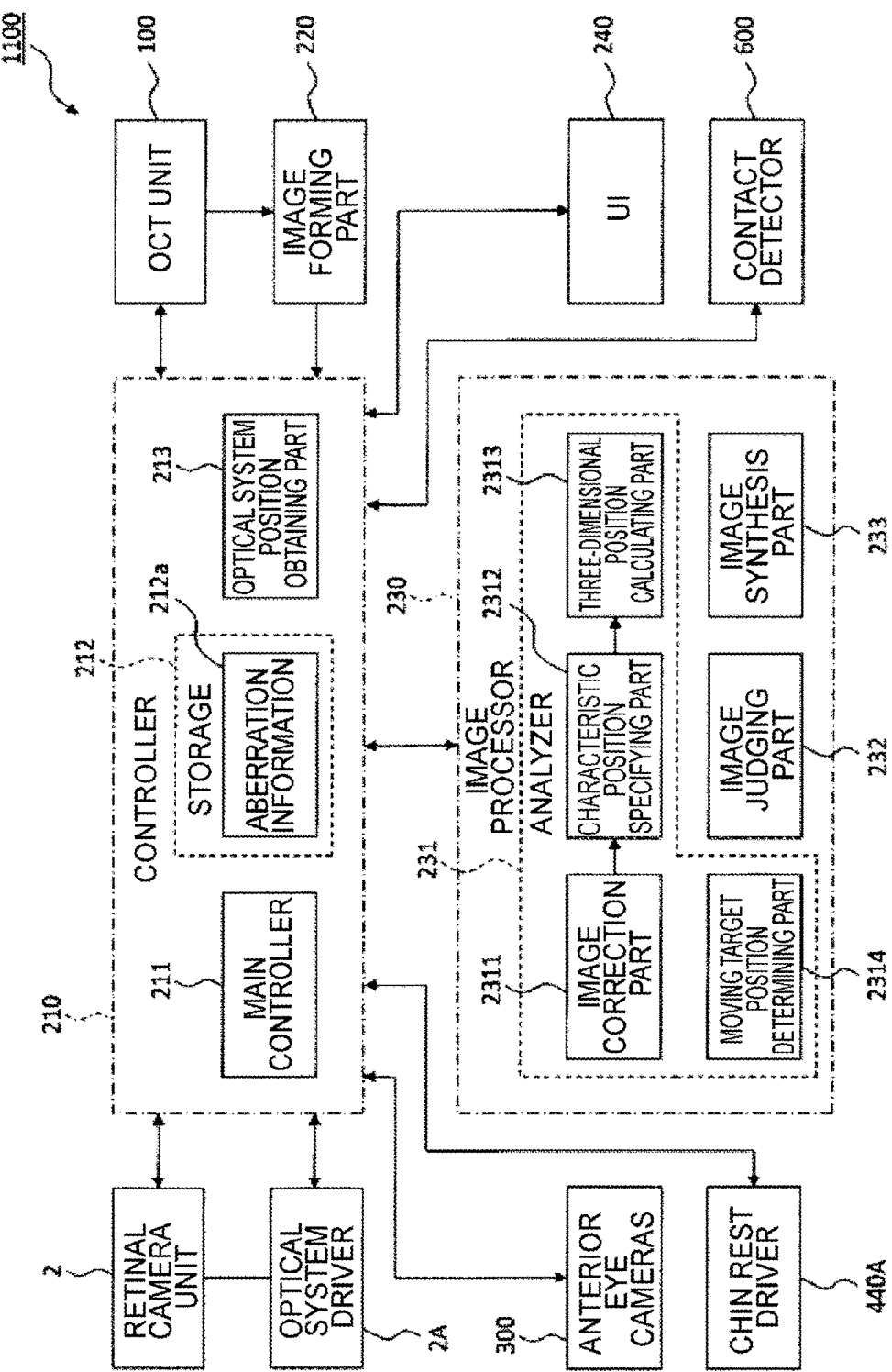
FIG. 13 is a schematic block diagram illustrating an example of a configuration of an ophthalmologic apparatus according to an modified example.

Modified examples of the present embodiment are described. An example of an ophthalmologic apparatus according to the present modified example is illustrated in FIG. 13. An ophthalmologic apparatus 1100 includes a contact detector 600. It should be noted that the approach detector 500 may be included in the ophthalmologic apparatus 1100 although it is not drawn in FIG. 13.

The contact detector 600 detects a state in which the face of the subject contacts with the supporting part 440. The contact detector 600 is arranged, for example, at a site of the supporting part 440 with which the face of the subject contacts (such as at middle position of the chin rest, at middle position of the forehead rest, etc.). The contact detector 600 has an arbitrary configuration that is capable of detecting contact of things. For example, the contact detector 600 may be configured to include a macro switch that can determine whether they are in contact or out of contact by switching electrical contact state/noncontact state of contacts.

When the detection result from the contact detector 600 indicates a contact state, that is, when the face contacts with the supporting part 440, the main controller 211 does not execute control of the chin rest driver 440A and only executes control of the optical system driver 2A. For example, when request for moving the supporting part 440 is input during a contact state, the main controller 211 does not execute movement of the supporting part 440 according to this movement request. Instead, the main controller 211 may execute notification that the movement request of the supporting part 440 cannot be received. On the other hand, when request for moving the examination optical system is input during a contact state, the main controller 211 may control the optical system driver 2A based on this movement request to move the examination optical system.

When the detection result from the contact detector 600 indicates an out-of-contact state, that is, when the face does not contact with the supporting part 440, the main controller 211 may execute bot controls of the optical system driver 2A and the chin rest driver 440A.

[Actions and Effects]

Actions and Effects of the ophthalmologic apparatuses (1000 and 1100) according to the present embodiment are explained. It should be noted that actions and effects given by configurations common to those in the first embodiment are the same as the actions and effects in the first embodiment; therefore, explanations of them are not repeated.

The ophthalmologic apparatus according to the present embodiment the chin rest driver 440A (the second driver) that moves the supporting part 440. The analyzer 231 analyzes two photograph images acquires by the anterior eye cameras 300A and 300B substantially simultaneously. The main controller 211 (the controller) controls the chin rest driver 440A based on the analysis results from the analyzer 231 to move the supporting part 440. According to the ophthalmologic apparatus thus configured, the supporting part 440 (and the examination optical system) may be relatively moved, thereby being capable of preferably executing position matching between the eye E of the subject whose face is supported by the supporting part 440 and the examination optical system.

The analyzer 231 may include the moving target position determining part 2314 that determines a moving target position of the supporting part 440 based on photograph images acquired by the anterior eye cameras 300A and 300B and positions of the anterior eye cameras 300A and 300B. If this is the case, the main controller 211 controls the chin rest driver 440A so as to move the supporting part 440 to the determined moving target position. Thereby, movement operation of the supporting part 440 may be carried out automatically.

The main controller 211 controls the chin rest driver 440A to move the supporting part 440 to a preset initial position when information indicating change of subjects is input. Such a configuration makes it possible to execute movement of the supporting part 440 from the preset position; therefore, position matching between the eye E and the examination optical system is carried out quickly.

The ophthalmologic apparatus according to the present embodiment may include the approach detector 500 that detects a state in which the subject approaches the supporting part 400. If this is the case, the main controller 211 may control the anterior eye cameras 300A and 300B to execute substantially simultaneous photography when the approach is detected. Thereby, it becomes possible to carry out imaging of the anterior eye part and processes executed upon receiving anterior eye images at preferable timing and automatically.

The ophthalmologic apparatus according to the present embodiment may include an inputting part and first storage. The inputting part is used for inputting identification information of a subject, and may be configured to include the operation part 240B and the main controller 211. The first storage may be configured to include the storage 211 and to associate, with the identification information of the subject, position information indicating a position of the examination optical system and/or position of the supporting part 440 having been applied in an examination, and store them. In the case of applying such a configuration, when identification information is input by the inputting part, the main controller 211 obtains position information that is associated this identification information from the first storage, and controls the optical system driver 2A and/or the chin rest driver 440A so as to move the examination optical system and/or the supporting part 440 to the position indicated in this position information. From such a configuration, it becomes possible to reproduce the position(s) of the examination optical system and/or the supporting part 440 applied in a past examination. Consequently, position matching between the eye E and the examination optical system is carried out quickly.

The ophthalmologic apparatus according to the present embodiment may include the contact detector 600 that detects a state in which the face of the subject contacts with the supporting part 440. If this is the case, the main controller 211 may be configured such that it is only capable of controlling the optical system driver 2A from among the optical system driver 2A and the chin rest driver 440A when the contact state is being detected by the contact detector 600. Further, the main controller 211 may be configured such that it is capable of controlling both of the optical system driver 2A and the chin rest driver 440A when the contact state is not being detected. According to such a configuration, it is possible to prohibit moving the supporting part 440 with which the face is being contacted.

The ophthalmologic apparatus according to the present embodiment may include the image judging part 232 (judging part) that analyzes a photograph image acquired by at least one of the anterior eye cameras 300A and 300B to judge whether or not an image of the anterior eye part is included in a preset region in this photograph image (in a frame). If this is the case, the main controller 211 may be configured to control the optical system driver 2A when the image of the anterior eye part is included in the preset region, and control the chin rest driver 440A when the image of the anterior eye part is not included in the preset region. According to such a configuration, it becomes possible to preferably use drive controls in a selective way in accordance with photographic images. For example, fine adjustment of position of the examination optical system may be carried out in the former case, and rough adjustment of position of the supporting part 440 may be carried out in the latter case.

Third Embodiment

Figure 14:
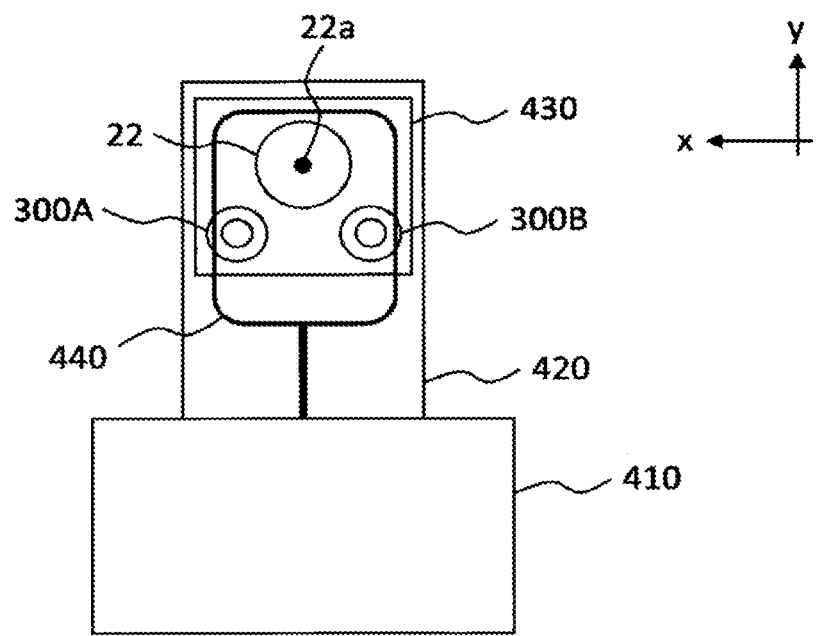
FIG. 14 is a schematic diagram illustrating an example of a configuration of an ophthalmologic apparatus according to an embodiment.

A characteristic of an ophthalmologic apparatus according to the present embodiment is arrangement of the imaging parts. A configuration example of the ophthalmologic apparatus according to the present embodiment is illustrated in FIG. 14.

Similar to the FIG. 4A of the first embodiment, symbol 410 indicates a base, symbol 420 indicates a case, symbol 430 indicates a lens case in which the objective lens 22 is housed, and symbol 440 indicates a supporting part.

In the present embodiment, the anterior eye cameras 300A and 300B are arranged at a lower positions (in the minus y-direction of) than a lens center 22a of the objective lens 22. The lens center 22a corresponds to a position through which the optical axis of the examination optical system of the ophthalmologic apparatus passes. Displacement in the y-direction between the lens center 22a and the anterior eye cameras 300A and 300B may be arbitrarily set by taking actions and effects described later into consideration. The anterior eye cameras 300A and 300B are arranged in a state in which optical axes thereof are tilted upward (tilted toward the eye E when examinations are carried out). An angle of inclination (angle of elevation) thereof may also be set arbitrarily.

Here, a meaning of "the imaging parts are provided at lower positions than the optical axis of the examination optical system" include not only a case in which whole imaging parts are arranged below the optical axis but also a case in which parts of the imaging parts are arranged at the same height level as the optical axis and a case in which parts of the imaging parts are arranged at higher positions than the optical axis. For example, if an outer dimension of the imaging parts is large, there are cases in which parts thereof are located at upper positions than the optical axis of the examination optical system. It should be noted that in any case, it is sufficient to set the relative position between the imaging parts and the examination optical system such that the optical axes of the imaging parts intersect a horizontal plane including the optical axis of the examination optical system from below.

According to the present embodiment, it becomes possible to reduce possibility of appearance of an eye lid and eyelashes in a photograph image acquired by the anterior eye cameras 300A and 300B (imaging parts). Further, even if a hollow about an eye (eye socket) of a subject is deep, anterior eye photography can be carried out, preferably.

Fourth Embodiment

There are cases in which a characteristic site (pupil center, corneal apex, etc.) of an anterior eye part cannot be detected from photograph images acquired by the imaging parts. Such a problem occurs in a case in which photography is carried out when eyelashes are depicted in photograph images or eye lids are insufficiently open, for example. Further, the characteristic site of the anterior eye cannot be detected in a case in which a field of imaging is shielded and preferable photograph image is not acquired due to a long nose or a deep eye socket of a subject. Further, there are cases in which preferable photograph images cannot be acquired in consequence of a make-up (such as an eye shadow, mascara, etc.). In the present embodiment, examples of processes that may be applied to cases in which the characteristic site of an anterior eye part cannot be detected from photograph images acquired by the imaging parts.

Figure 3:
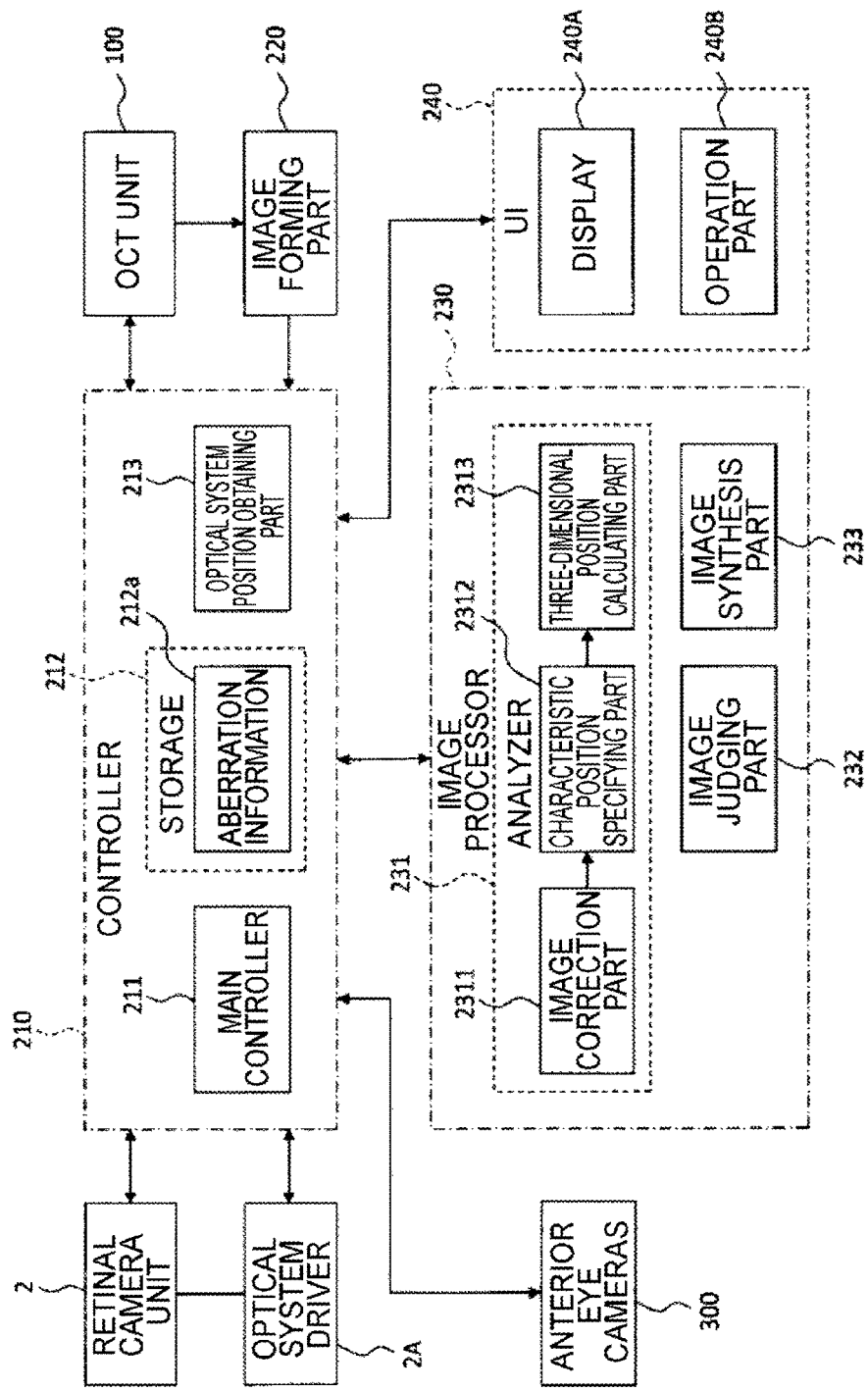
FIG. 3 is a schematic block diagram illustrating an example of a configuration of an ophthalmologic apparatus according to an embodiment.
Figure 15:
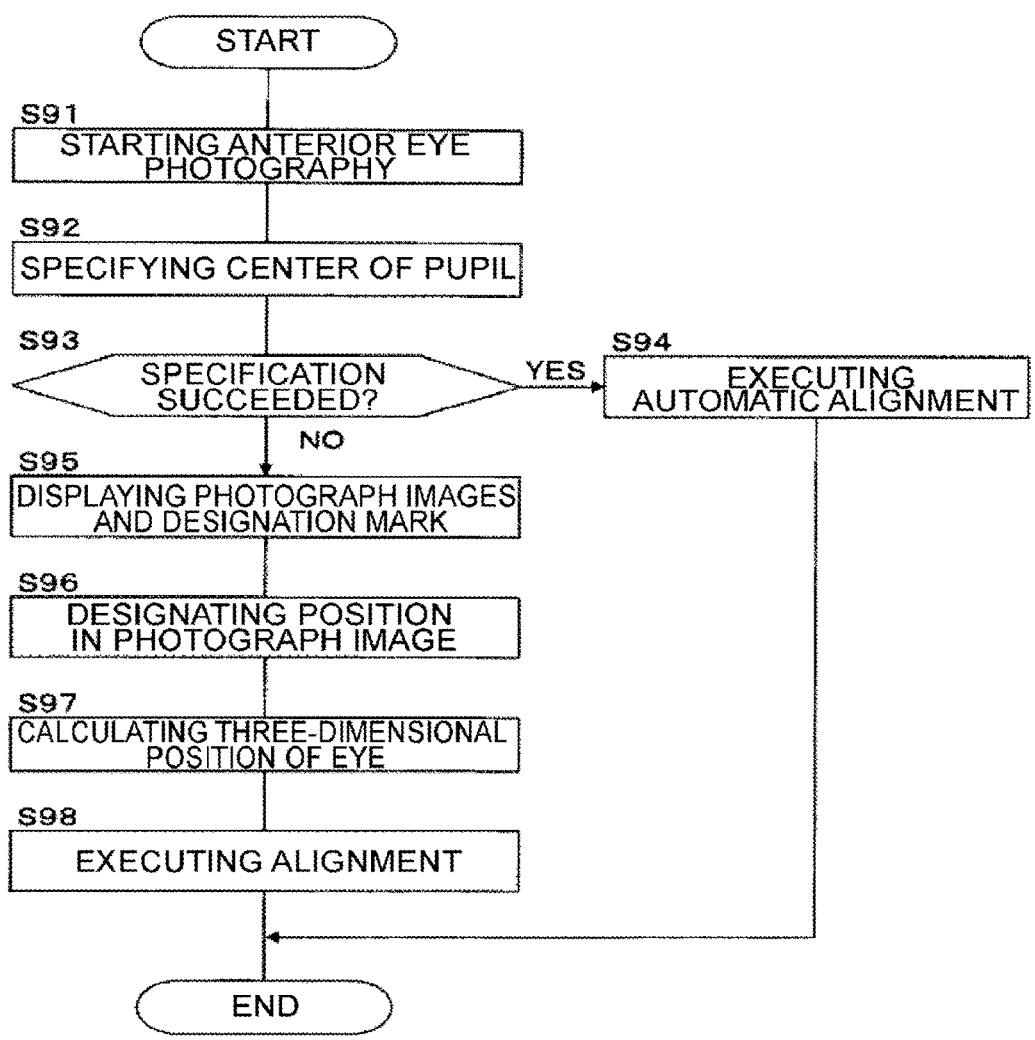
FIG. 15 is a flowchart illustrating an operational example of an ophthalmologic apparatus according to an embodiment.

An ophthalmologic apparatus according to the present embodiment includes a configuration similar to that in the first embodiment, for example (in particular, FIG. 3 is referred to). FIG. 15 indicates an operation example of the ophthalmologic apparatus according to the present embodiment. It should be noted that the patient registration, selection of photography type, and operation for starting automatic alignment have been done already.

(S91: Starting Anterior Eye Photography)

The controller 210 controls the anterior eye cameras 300A and 300B to commence photographing of the anterior eye part Ea. This photography is moving image photography of the anterior eye part Ea as the photography subject. The controller 210 displays images acquired in time-series on the display 240A as a moving image.

(S92: Specifying Center of Pupil)

The image correction part 2311 corrects the distortion of each frame transmitted from the controller 210 based on the aberration information 212a stored in the storage 212. The pair of frames with the distortion thereof corrected is transmitted to the characteristic position specifying part 2312.

The characteristic position specifying part 2312 analyzes each frame transmitted from the image correction part 2311, thereby carrying out the process for specifying the characteristic position in the frame corresponding to the characteristic site (here, center of the pupil is adopted) of the anterior eye part Ea.

(S93: Specification Succeeded?)

If the specification of the characteristic position has been successful (S93: YES), the characteristic position specifying part 2312 transmits information indicating this result to the controller 210, and the process is transferred to Step S94. On the other hand, In the event of failure in specifying the characteristic position (S93: NO), the characteristic position specifying part 2312 transmits information indicating this result to the controller 210, and the process is transferred to Step S95.

(S94: Executing Automatic Alignment)

If the specification of characteristic position has been successful (S93: YES), the controller 210 controls the respective parts of the apparatus to carry out automatic alignment. This automatic alignment includes processes indicated in Step S8 to Step S11 of FIG. 6 in the first embodiment. Automatic alignment in this case is terminated here.

(S95: Displaying Photograph Images and Designation Mark)

If the specification of characteristic position has failed (S93: NO), the controller 210 displays photograph images acquired by one or both of the anterior eye cameras 300A and 300B on the display 240A. Further, the controller 210 displays a designation mark for assisting the user to designate an image position on the display 240A.

The designation mark is described. The designation mark is an image indicating a position in a photograph image and has a predetermined shape (point-shaped, cross-shaped, arrow-shaped, etc.). The designation mark may be displayed all the time, or may be displayed upon the user designates an image position in latter Step S96.

Display of photograph images is described. At the stage of transferring to Step S95, display of a moving image started in Step S91 is being executed. This movie display may be continued until display of photograph images in Step S95. Alternatively, this movie display may be switched to another display mode. As an example of this, it is possible to display a single frame from among frames used in this movie display. In short, it may be switched to still-image display. The frame displayed is a frame displayed at a timing of transition to Step S95, for example.

Another example of switching of display modes is described. The controller 210 may selectively display one of photograph images acquired by the respective anterior eye cameras 300A and 300B. This process is executed in the following way, for example.

Firstly, the controller 210 analyzes respective photograph images acquired by the anterior eye cameras 300A and 300B to evaluate image quality of the photograph images. This image quality evaluation may include evaluation of existence or degree of flare, evaluation of appearance of eyelashes etc., evaluation of morphology (shape, size) of an image of an iris (and pupil), for example. This "evaluation of image quality" is a process of evaluating a predetermined factor indicating whether or not a concerned image is suitable for observation or indicating the extent of suitability for observation.

The image quality process includes contents in accordance with applied factors. For example, the evaluation of flare may include: a process of judging whether or not an image region in which pixel values (brightness values) is equal to or larger than a preset threshold exists; a process of calculating differences between pixel values and a preset threshold; and/or a process of evaluating image quality based on the result of this judgment and the result of this calculation. Further, the evaluation of appearance of eyelashes etc. may include: a process of specifying image regions corresponding to eyelashes etc. (sites other than the anterior eye part Ea) based on pixel values; a process of specifying an overlapping state of the image regions of the eyelashes etc. and the image region of the anterior eye part Ea; and a process of evaluating image quality based on the overlapping state specified. Further, the evaluation of an image of iris (and pupil) may include: a process of specifying image regions corresponding to iris (and pupil); a process of obtaining morphology information of this image region; and a process of evaluating image quality based on the morphology information obtained.

The controller 210 selects a single photograph image from among photograph images acquired by the anterior eye cameras 300A and 300B based on the result of evaluation of image quality. A photograph image selected may be a still image or a moving image. The controller 210 displays the selected photograph image on the display 240A.

(S96: Designating Position in Photograph Image)

The user observes the photograph image displayed in Step S95 and designates an image position corresponding to a characteristic site (pupil center). This designating operation is performed using the operation part 240B. As an example of the designating operation, an operation for moving the designation mark to a desired location may be performed by using the operation part 240B. As another example of the designating operation, in the case in which the display 240A includes a touch panel (that is, the display 240A and the operation part 240B are configured integrally), the user touches a desired location in the displayed photograph image. Once an image position in the photograph image is designated, the user performs an operation for confirming the designation result by using the operation part 240B. The controller 210 obtains position information indicating the image position designated. This position information is a coordinate in a coordinate system defined for the photograph image, for example.

It should be noted that instead of designating an image position by displaying one photograph image as described above, a configuration may be adopted in which a pair of photograph images acquired by the anterior eye cameras 300A and 300B are displayed and image positions are designated in both of the photograph images. If this is the case, for example, the average position of the two designated positions, that is, the coordinate at the middle between the two designated positions may be used as the designation result to criate position information.

(S97: Calculating Three-Dimensional Position of Eye)

The three-dimensional position calculating part 2313 calculates a three-dimensional position of the characteristic site (pupil center) of the anterior eye part Ea based on positions of the anterior eye cameras 300A and 300B and the image position designated in Step S96. This process is carried out, for example, by executing a similar process using the image position designated in Step S96 instead of the characteristic position specified by the characteristic position specifying part 2312 in Step S9 of FIG. 6 in the first embodiment. Here, such an alternative application may be easily carried out since the above position information is a coordinate in the coordinate system defined for photograph images.

In Step S96, if an image position is designated only for a photograph image acquired by one of the anterior eye cameras 300A and 300B, the three-dimensional position calculating part 2313 specifies a corresponding position in a photograph image acquired by the other. Examples of this process are described. Firstly, the three-dimensional position calculating part 2313 executes image position matching on both photograph images to associate coordinate systems of the both photograph images (that is, it obtains a coordinate transformation between these coordinate systems). The three-dimensional position calculating part 2313 specifies an image position in the other photograph image corresponding to the designated position in one photograph image based on the coordinate transformation. The three-dimensional position calculating part 2313 calculates a three-dimensional position of the characteristic site (pupil center) of the anterior eye part Ea based on positions of the anterior eye cameras 300A and 300B, the image position designated in one photograph image and the image position specified in the other photograph image.

(S98: Executing Alignment)

The controller 210 executes alignment of the examination optical system with respect to the eye E based on the three-dimensional position of the pupil center calculated in Step S97. This alignment may be executed in a way similar to Step S10 (movement of the examination optical system) and Step S11 (process of determining convergence of position) of FIG. 6 in the first embodiment.

According to the present embodiment, it becomes possible to carry out alignment using a position designated by the user when a characteristic site (pupil center, corneal apex, etc.) of the anterior eye part cannot be detected from photograph images. Consequently, alignment may be carried out smoothly and quickly even when a characteristic site cannot be detected.

Modified Examples

An image position specified by the characteristic position specifying part 2312 may be treated as a candidate for a characteristic position corresponding to a characteristic site of the anterior eye part Ea. Operation examples of such a case are described.

The characteristic position specifying part 2312 executes the same processes as in the first embodiment to specify a candidate position of a characteristic position corresponding to a characteristic site. The number of candidate positions specified is one or more than one.

The controller 210 displays photograph images on the display 240A and displays information (candidate position information) indicating each candidate position specified by the characteristic position specifying part 2312. The candidate position information is, for example, an image indicating a position (coordinate) in a photograph image corresponding to a candidate position, and is of a predetermined shape (point-shaped, cross-shaped, arrow-shaped, etc.).

The user designates desired candidate position information from among displayed candidate position information. This designation is carried out by using the operation part 240B. The three-dimensional position calculating part 2313 calculates a three-dimensional position of the characteristic site of the anterior eye part Ea based on the coordinate of the designated candidate position information and positions of the anterior eye cameras 300A and 300B.

It should be noted that when a candidate position is designated only to one of the photograph images, processes similar to those in the first embodiment may be executed. Further, it may be configured to move displayed candidate position information arbitrarily in the same manner as in the above embodiments.

In the present modified example, if only single candidate position information is displayed, an operation for designation performed by the user corresponds to judgment whether or not this candidate position is approved. If not approved, the user carries out a predetermined operation. Upon receiving this operation the controller 210 may switch operation mode to the process described in the above embodiments (FIG. 15).

On the other hand, if two or more candidate position information are displayed, an operation for designation performed by the user corresponds to selection of candidate positions. When none of the candidate positions is selected, the user performs a predetermined operation. Upon receiving this operation, the controller 210 may switch operation mode to the process described in the above embodiments (FIG. 15).

According to the present modified example, a candidate of a characteristic position corresponding to a characteristic site of the anterior eye part Ea may be selected by the user, thereby being capable of improving accuracy and smoothness of alignment.

Fifth Embodiment

As explained in the above embodiments, there are cases in which alignment cannot be carried out preferably due to conditions of anterior eye photography. For example, there are cases in which flare appears in a photograph image of an anterior eye part because of individual differences of eyes (shape of a cornea, distance between a cornea and a lens, etc.). If such problems cannot be resolved, manual alignment may be carried out. Manual alignment is performed by searching a preferable alignment position while observing an image of an eye. However, manual alignment greatly depends on experiences and levels of skills of users. Therefore, reproducibility of alignment is low and unevenness due to skills becomes large. The present embodiment describes ophthalmologic apparatuses realized by focusing on such problems.

Figure 16:
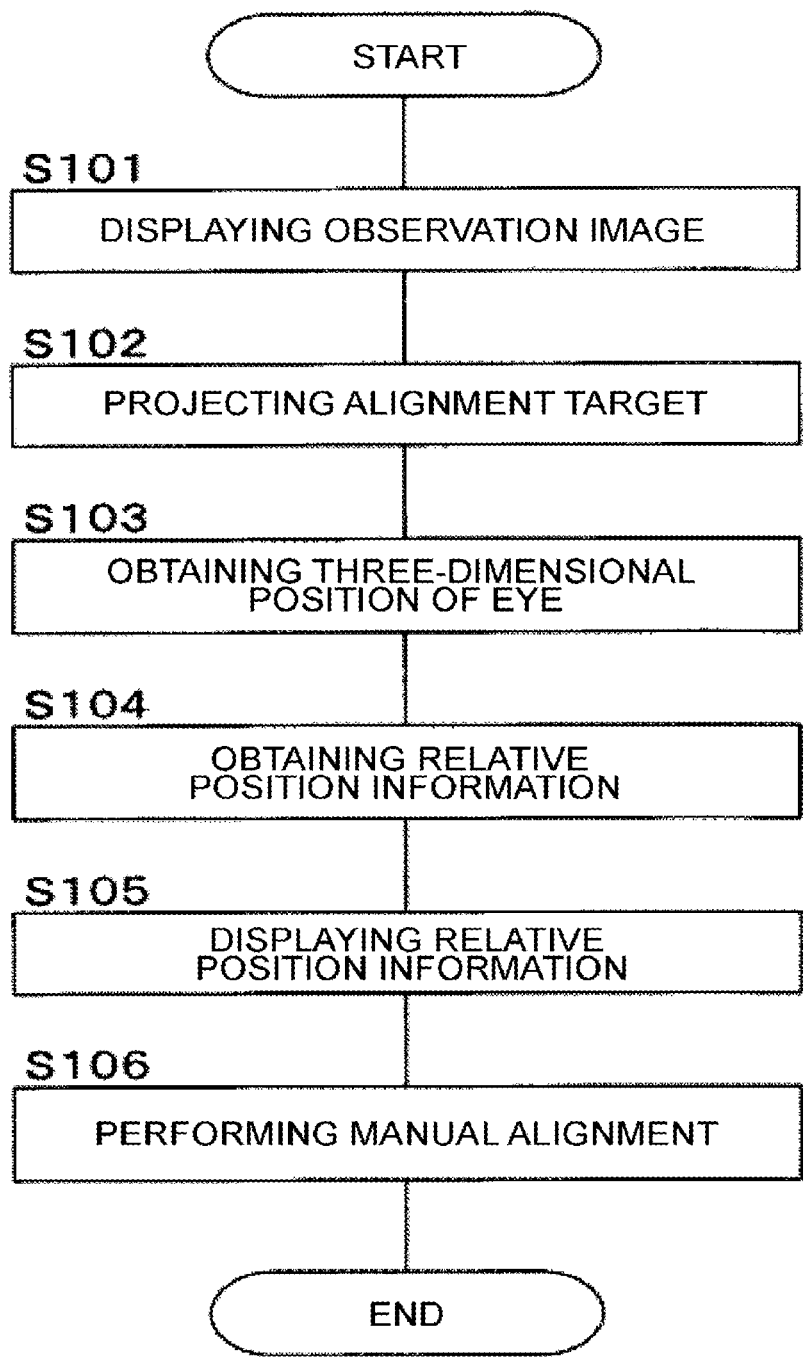
FIG. 16 is a flowchart illustrating an operational example of an ophthalmologic apparatus according to an embodiment.

An ophthalmologic apparatus according to the present embodiment includes a configuration similar to the above embodiments (in particular, FIG. 3 is referred to). Particularly, the ophthalmologic apparatus according to the present embodiment includes the alignment optical system 50 that projects the alignment target onto the eye E. An operation example of the ophthalmologic apparatus according to the present embodiment is illustrated in FIG. 16. It should be noted that patient registration and selection of photography type have already been carried out. Further, when an alignment mode explained in the above embodiments has not been carried out preferably, an operation mode illustrated in FIG. 16 may be executed. Alternatively, the operation mode illustrated in FIG. 16 may be executed from the beginning of examination.

(S101: Displaying Observation Image)

Firstly, the controller 210 controls the retinal camera unit 2 to acquire an observation image (moving image) of the eye E, and display, as a moving image, the observation image acquired in time-series on the display 240A in real time.

(S102: Projecting Alignment Target)

The controller 210 controls the alignment optical system 50 to project the alignment target onto the eye E. It should be noted that timings of executing Step S101 and Step S102 are arbitrary. Upon Step S101 and Step S102 are executed, an image of the alignment target comes to be depicted in the observation image displayed. Further, the controller 210 displays information for assisting execution of alignment together with the observation image. Examples of such information include an image indicating a guidepost position of the alignment target whose displayed position moves in accordance with movement of the examination optical system.

(S103: Obtaining Three-Dimensional Position of Eye)

The controller 210 controls the anterior eye cameras 300A and 300B to acquire photograph images. The analyzer 231 obtains a three-dimensional position of the eye E based on the acquired photograph images. This process may be carried out in a way similar to the first embodiment.

(S104: Obtaining Relative Position Information)

The controller 210 obtains relative position information indicating a relative position between the eye E and the examination optical system based on the three-dimensional position of the eye E obtained in Step S103. This process may be executed in the following way, for example. Firstly, the controller 210 obtains a current position of the examination optical system. The current position is obtained from a history of control of the optical system driver 2A that moves the retinal camera unit 2, for example. Further, it may be configured to provide a position sensor that detects a position of the retinal camera unit 2 and obtain the current position from results of detection by this position sensor. Here, it is assumed that a coordinate system defining the three-dimensional position (coordinate) of the eye E obtained in Step S103 and a coordinate system defining the current position (coordinate) of the examination optical system are common. Alternatively, it is assumed that a coordinate transformation between these coordinate systems is known.

The relative position information is explained. The relative position information is information indicating the relative position between the eye E and the examination optical system as described above. Examples of the relative position include a position of one of the eye E and the examination optical system with respect to the other, a difference between the position of the eye E with respect to a preset standard position and the position of the examination optical system with respect to the same standard position (difference of vectors, difference of coordinates), etc.

Further, although equivalent to these, a displacement of the examination optical system with respect to an alignment destination position is treated as the relative position information in the present embodiment. The alignment destination position is a position of the examination optical system suitable for examinations of the eye E; that is, a position at which the axis of the eye E and the optical axis of the examination optical system are aligned in the x-direction (left/right direction) and the y-direction (vertical direction) and at which the examination optical system is away from the eye E by a preset working distance in the z-direction (front/rear direction, optical-axis direction). Since the working distance is known and the three-dimensional position of the eye E is obtained in Step S103, it is possible to obtain a coordinate of the alignment destination position in the common coordinate system, for example. Such relative position information includes a relative position in the direction along the optical axis of the examination optical system, a relative position in the horizontal direction, and a relative position in the vertical direction, wherein the horizontal and vertical directions are perpendicular to the optical axis of the examination optical system.

(S105: Displaying Relative Position Information)

The controller 210 displays the relative position information obtained in Step S104 on the display 240A. Examples of display modes of the relative position information are described below.

As a first example, the controller 210 may display numerical values indicating the displacements in the x-direction, the y-direction and the z-direction. If this is the case, the controller 210 may display the numerical values in three display spaces provided inside or outside a region in which the observation image is displayed, for example.

Similarly, character string information indicating the displacements may be displayed. For example, when the displacement in the x-direction exists on the left of the alignment destination position, character string information indicating this fact may be displayed.

As a second example, the controller 210 may display images indicating the displacements in the x-direction, the y-direction and the z-direction. If this is the case, the controller 210 may display an image indicating the alignment destination position and further display images indicating the displacements of the respective directions relative to this alignment destination position at locations according to the displacements. For example, when the current position of the examination optical system is located at the upper left of the alignment destination position, an image (for example, a point-shaped image) indicating the displacements in the x-direction and the y-direction may be displayed at the upper left of the image indicating the alignment destination position. Here, the distance between the display positions of the both images are determined based on a displacement in the xy-plane.

In the second example, since the observation image is an image photographed the eye E from the front, it is easily to display the displacements in the x-direction and the y-direction such that they are intuitively recognizable. Further, regarding the z-direction (optical-axis direction), it is needed to devise a way such that the displacement becomes intuitively recognizable. As an example of this, the controller 210 may display the displacement (relative position) in the z-direction with a preset color. Specifically, it may be configured, for example: to display an image indicating the displacement in the z-direction in green when the displacement in the z-direction is within a preset allowable range including the alignment destination position; to display the image in red when the displacement is smaller than the minimum of the allowable range; and to display the image in yellow when the displacement is larger than the maximum of the allowable range. Further, in order to indicate the amount of the displacement in addition to the direction of the displacement, it is possible to vary density of display color of the image indicating the displacement in the z-direction, or display the numerical values or images in the first example together with the image indicating the displacement in the z-direction.

As a third example, information (character string information, image) indicating a direction in which the examination optical system should be moved and/or the amount by which the examination optical system should be moved may be displayed. As an example of the character string information, when the optical axis of the examination optical system is displaced by 1 cm to the right from the alignment destination position, information "left: 1 cm" indicating the direction and the amount of movement of the examination optical system for cancelling this displacement. As an example of the image, in a similar case, an arrow indicating the direction of movement of the examination optical system (an arrow pointing to the left) may be displayed. Here, it may be configured to indicate the movement amount by the length of the arrow, for example.

(S106: Performing Manual Alignment)

The user refers to the observation image and the relative position information displayed and operates the operation part 240B, thereby moving the examination optical system.

Here, the controller 210 may change display mode of the relative position information in accordance with contents of movement of the examination optical system. For example, the controller 210 obtains the relative position information again in real time in accordance with contents of movement of the examination optical system, and displays the new relative position information in real time. Thereby, display of the above numerical values, character strings and images are updated in real time. As a specific example, when the position of the examination optical system in the z-direction is gradually approaching the alignment destination position (working distance) by user's operation, display color of the image indicating the displacement in the z-direction changes from yellow to green.

According to the ophthalmologic apparatus according to the present embodiment, it is possible to present the position of the examination optical system relative to the eye E, that is, a position gap of the examination optical system relative to the alignment destination position based on the highly accurate three-dimensional position of the eye E calculated from photograph images acquired by the anterior eye cameras 300A and 300B. Therefore, alignment can be carried out based on quantitative information without depending on user's experiences and levels of skills. Consequently, it is possible to improve reproducibility of alignment and prevent unevenness due to skills.

It should be noted that accuracy of manual alignment may be further improved by referring eye information. The eye information is, for example, measurement information indicating characteristic of the eye E that has been obtained from a previously performed examination of the eye E. This measurement information may be obtained by this ophthalmologic apparatus or other ophthalmologic apparatus. The measurement information is previously associated with a patient ID etc. and stored in the storage 212, for example.

The controller 210 selects measurement information corresponding to the eye E based on patient ID etc. Further, the controller 210 generates the relative position information based on the selected measurement information and the three-dimensional position of the eye E obtained by the analyzer 231. As an example of this process, the relative positions in the x-direction and the y-direction may be corrected based on distortion of the shape of the cornea. Further, the relative position in the z-direction may be corrected based on an axial length of the eye E. The latter is especially effective in a case of examinations of eye fundus.

Generation of the relative position information by taking measurement information of the eye E into consideration makes it possible to obtain and present the relative position information with higher accuracy corresponding to individual differences of eyes.

Sixth Embodiment

Conventional ophthalmologic apparatuses execute alignment by projecting an alignment target onto a cornea and moving an examination optical system so as to locate a projection image thereof at a predetermined position. However, embodiments of the present invention execute alignment by obtaining a three-dimensional position of an eye from analysis of two or more photograph images acquired by two or more imaging parts substantially simultaneously, and moving an examination optical system and/or a supporting part based on this three-dimensional position.

Here, the analysis for obtaining the three-dimensional position of the eye is carried out based on an iris, pupil, etc. depicted in the respective photograph images. Therefore, it is desirable to carry out alignment by considering the iris (or the pupil that is an opening formed by the iris) as a reference instead of considering the cornea as a reference as in conventional ways. The present embodiment describes a technology for improving accuracy of alignment (in the z-direction) in which an iris (or pupil) is used as a reference. Hereinafter, FIG. 3 illustrating a configuration of the first embodiment is referred to for explanation.

The storage 212 previously stores distance information indicating a distance between a cornea and an iris (pupil). The distance indicated in the distance information may be obtained by an arbitrary method. For example, the distance may be a standard distance based on a schematic eye (such as the Gullstrand eye model), a statistical distance based on measurement results obtained from multiple eyes, individual distance obtained by measuring the concerned eye in the past, etc.

It should be noted that measurement of distance between a cornea and an iris may be carried out in the following manner, for example. Firstly, an anterior eye tomographic image is acquired by performing OCT measurement to an anterior eye of an eye. Next, by analyzing this anterior eye tomographic image, an image region corresponding to the cornea (cornea region) and an image region corresponding to the iris (iris region) are extracted. Then, a distance between the cornea and the iris is calculated by, for example, counting the number of pixels between the cornea region (posterior surface of the cornea) and the iris region (anterior surface of the iris). Here, this distance is a distance along the z-direction. Such a measurement may be carried out by the ophthalmologic apparatus 1 itself or by other apparatuses.

The characteristic position specifying part 2312 of the analyzer 231 specifies a characteristic position corresponding to the iris (pupil) from the respective photograph images acquired by the anterior eye cameras 300A and 300B as in the first embodiment.

The three-dimensional position calculating part 2313 calculates a three-dimensional position of the concerned characteristic site based on positions of the anterior eye cameras 300A and 300B and the characteristic position specified by the characteristic position specifying part 2312. In this process, the distance information stored in the storage 212 may be referred to. For example, if a distance between the cornea (corneal apex) of the eye E and the examination optical system may be obtained, addition of this distance and the distance indicated by the distance information makes it possible to obtain an distance between the examination optical system and the iris with high accuracy. It should be noted that the distance between the cornea and the examination optical system may be obtained from a conventional alignment method carried out by using the alignment optical system 50 illustrated in FIG. 1.

Further, the distance between the examination optical system and the cornea (corneal apex) may be obtained by subtracting the distance indicated in the distance information from the distance between the iris (pupil) and the examination optical system obtained in the same way as in the first embodiment. Then, alignment in the z-direction may be carried out by using the distance thus obtained.

Modified Example

Configurations described above are merely examples for preferably implementing the present invention. Therefore, arbitrary modifications (omission, replacement, addition, etc.) may be applied within the scope of the invention.

In the above embodiments, the main controller 211 may display a synthetic image formed by the image synthesis part 233 on the display 240A. Thereby, stereoscopic morphology of an anterior eye part may be observed.

In the above embodiments, the main controller 211 may display at least one of two photograph images substantially simultaneously acquired by the anterior eye cameras 300A and 300B on the display 240A. Thereby, morphology of an anterior eye part may be observed from different viewpoints (photographing positions).

If light used for examinations by the ophthalmologic apparatus 1 appears in photograph images, there is a risk of giving influence to image processing of the photograph images. For example, since intensity of light from an LED or an SLD provided in the ophthalmologic apparatus 1 is relatively high, image processing may not be executed properly if such light appears in photograph images. In order to solve such a problem, filters that are configured to intercept light of wavelengths other than those of environmental illumination may be provided at positions between the respective anterior eye cameras 300 (two or more imaging parts) and the eye E. The environmental illumination means an illumination used in an environment in which the ophthalmologic apparatus 1 is located. For example, an illumination provided in a room in which the ophthalmologic apparatus 1 is installed corresponds to the environmental illumination. Further, the environmental illumination may contain sunlight. It should be noted that taking purposes of this configuration into consideration, the filters may be configured to intercept wavelengths giving influence to photography using the anterior eye cameras 300 from among wavelengths contained in the environmental illumination. For example, the filters may be configured to intercept wavelength components (such as wavelengths output from the LED, SLD, etc.) used in examinations by the ophthalmologic apparatus 1 from among wavelengths contained in the environmental illumination. As a specific example, filters intercepting wavelengths equal to or shorter than 900 nm may be applied. According to such configurations, it is possible to avoid influence of disturbance applied to photography using the anterior eye cameras 300, thereby acquiring photograph images in which a characteristic site (pupil etc.) of an anterior eye part is clearly depicted. Consequently, analysis for specifying a characteristic position (center of pupil etc.) in photograph images may be carried out preferably.

In the above embodiments, the difference in optical path length between the optical path of the signal light LS and the optical path of the reference light LR is changed by changing the position of the optical-path-length changing part 41; however the method for changing the difference in optical path length is not limited to this. For example, it is possible to change the difference in optical path length by providing a reflection mirror (reference mirror) in the optical path of the reference light, and moving this reference mirror along the propagation direction of the reference light to change the optical path length of the reference light. Moreover, it is possible to change the optical path length of the signal light LS by moving the retinal camera unit 2 and/or the OCT unit 100 relative to the eye E, thereby changing the difference in optical path length. Moreover, particularly if the object being measured is not a region of a living body, it is possible to change the difference in optical path length by moving the object being measured in the depth direction (z-direction).

Computer programs for realizing the above embodiments can be stored in any kind of recording medium that can be read by a computer. As this recording medium, for example, a semiconductor memory, an optical disk, a magneto-optic disk (CD-ROM, DVD-RAM, DVD-ROM, MO, and so on), and a magnetic storage (a hard disk, a Floppy Disk™, ZIP, and so on) can be used.

Further, it may be configured to transmit/receive this program through networks such as the internet, a LAN, etc.

EXPLANATION OF SYMBOLS 1, 1000, 1100 ophthalmologic apparatus
2 retinal camera unit
2A optical system driver
10 illumination optical system
30 imaging optical system
31 focusing lens
41 optical-path-length changing part
42 galvano scanner
50 alignment optical system
60 focus optical system
100 OCT unit
101 light source unit
105 optical attenuator
106 polarization adjuster
115 CCD image sensor
200 arithmetic and control unit
210 controller
211 main controller
212 storage
212a aberration information
213 optical system position obtaining part
220 image forming part
230 image processor
231 analyzer
2311 image correction part
2312 characteristic position specifying part
2313 three-dimensional position calculating part
2314 moving target position determining part
232 image judging part
233 image synthesis part
240A display
240B operation part
300, 300A, 300B anterior eye camera(s)
410 base
420 case
430 lens case
440 supporting part
440A chin rest driver
500 approach detector
600 contact detector
E eye
Ea anterior eye part
Ef fundus
LS signal light
LR reference light
LC interference light

What is claimed is:
1. An ophthalmologic apparatus comprising:
an examination optical system configured to carry out an examination of an eye;
a supporting part configured to support a face of a subject;

a driver configured to move the examination optical system and the supporting part relatively and three-dimensionally;

two or more imaging parts configured to substantially simultaneously photograph an anterior eye part of the eye from different directions;

an analyzer configured to obtain a three-dimensional position of the eye by analyzing two or more photograph images acquired by the two or more imaging parts substantially simultaneously; and a controller configured to control the driver based on the three-dimensional position to relatively move the examination optical system and the supporting part in order that a position of the examination optical system and the three-dimensional position of the eye match each other in two axis directions both perpendicular to an optical axis direction of the examination optical system, and a distance between the examination optical system and the eye becomes a predetermined working distance in the optical axis direction, wherein the analyzer comprises:
 a characteristic position specifying part configured to analyze the two or more photograph images to specify characteristic positions in the photograph images that correspond to a predetermined characteristic part of the anterior eye part; and
 a three-dimensional position calculating part configured to calculate, as the three-dimensional position of the eye, a three-dimensional position of the characteristic part based on positions of the two or more imaging parts and the characteristic positions in the two or more photograph images.

2. The ophthalmologic apparatus of claim 1, wherein
the driver comprises a first driver configured to move the examination optical system three-dimensionally, and
the controller controls the first driver based on the three-dimensional position to align the optical axis of the examination optical system with an axis of the eye and adjust a distance between the eye and the examination optical system to a preset working distance.

3. The ophthalmologic apparatus of claim 2, further comprising:
a moving-image acquiring optical system configured to acquire a moving image of the anterior eye part of the eye, wherein a part of its optical path is shared with the examination optical system;
a projecting optical system configured to project a target for executing position matching of the examination optical system with the eye onto the eye; and
an operation part, wherein
when the characteristic position has not been specified by the characteristic position specifying part, the controller controls the projecting optical system to project the target onto the eye, controls the moving-image acquiring optical system to acquire a moving image of the anterior eye part onto which the target is being projected, controls a display to display the acquired moving image, and controls the first driver to move the examination optical system in accordance with an operation carried out by using the operation part.

4. The ophthalmologic apparatus of claim 3, wherein
after the examination optical system is moved by using the operation part, the characteristic position specifying part specifies an image position in the moving image that corresponds to the characteristic part, and
the controller displays information indicating the specified image position over the moving image.

5. The ophthalmologic apparatus of claim 1, wherein the characteristic part is a center of a pupil or a corneal apex of the anterior eye part.

6. The ophthalmologic apparatus of claim 1, further comprising
an operation part, wherein
the controller displays at least one of the two or more photograph images on a display, and
when the characteristic position has not been specified by the characteristic position specifying part, the three-dimensional position calculating part calculates the three-dimensional position of the characteristic part based on the positions of the two or more imaging parts and an image position designated in the displayed photograph image by using the operation part.

7. The ophthalmologic apparatus of claim 6, wherein when the image position is designated in one of the two or more photograph images, the three-dimensional position calculating part specifies image positions in other photograph images that correspond to this designated image position and calculates the three-dimensional position of the characteristic part based on the positions of the two or more imaging parts, the designated image position, and the specified image positions.

8. The ophthalmologic apparatus of claim 6, wherein the controller analyzes the two or more photograph images to evaluate image quality of the photograph images and selects one photograph image based on the evaluation results of the image quality to display it on the display.

9. The ophthalmologic apparatus of claim 1, further comprising
an operation part, wherein
the characteristic position specifying part analyzes the two or more photograph images to specify one or more candidate positions of the characteristic position,
the controller displays at least one of the two or more photograph images and candidate position information indicating the specified candidate positions on a display, and
the three-dimensional position calculating part calculates the three-dimensional position of the characteristic part based on the positions of the two or more imaging parts and a candidate position corresponding to candidate position information that is designated by using the operation part from among the one or more candidate position information displayed.

10. The ophthalmologic apparatus of claim 2, wherein the controller comprises an optical system position obtaining part configured to obtain a current position of the examination optical system, and controls the first driver based on the obtained current position and the three-dimensional position of the eye obtained by the analyzer to move the examination optical system.

11. The ophthalmologic apparatus of claim 2, wherein
the two or more imaging parts acquire moving images of the anterior eye part of the eye from different directions in parallel,
the analyzer successively analyzes two or more frames acquired substantially simultaneously in this moving image acquisition to obtain the three-dimensional positions of the eye successively, and
the controller successively controls the first driver based on the three-dimensional positions successively obtained to make the position of the examination optical system follow movement of the eye.

12. The ophthalmologic apparatus of claim 2, wherein
the driver comprises a second driver configured to move the supporting part, and
the controller controls the second driver based on the analysis results of the two or more photograph images from the analyzer to move the supporting part.

13. The ophthalmologic apparatus of claim 12, wherein the second driver moves the supporting part at least in a vertical direction.

14. The ophthalmologic apparatus of claim 12, wherein
the analyzer comprises a moving target position determining part configured to determine a moving target position of the supporting part based on the two or more photograph images and positions of the two or more imaging parts, and
the controller controls the second driver to move the supporting part to the moving target position.

15. The ophthalmologic apparatus of claim 12, wherein the controller controls the second driver to move the supporting part to a preset initial position when information indicating change of subjects is input.

16. The ophthalmologic apparatus of claim 12, further comprising an approach detector configured to detect a state in which the subject approaches the supporting part, wherein
when the approach is detected, the controller controls the two or more imaging parts to execute substantially simultaneous photography.

17. The ophthalmologic apparatus of claim 12, further comprising:
an inputting part configured to input identification information of a subject; and
a first storage configured to store position information indicating a position of the examination optical system and/or a position of the supporting part applied in an examination wherein the position information is associated with the identification information of a subject concerned, wherein
when identification information is input by the inputting part, the controller obtains position information associated with this identification information from the first storage, and controls the first driver and/or the second driver to move the examination optical system and/or the supporting part to the position indicated in the obtained position information.

18. The ophthalmologic apparatus of claim 12, further comprising a contact detector configured to detect a state in which the face of the subject contacts with the supporting part, wherein
while the contact is being detected, the controller is configured to control the first driver only from among the first driver and the second driver.

19. The ophthalmologic apparatus of claim 18, while the contact is not being detected, the controller is configured to control both of the first driver and the second driver.

20. The ophthalmologic apparatus of claim 12, further comprising a judging part configured to analyze a photograph image acquired by at least one of the two or more imaging parts to judge whether or not an image of the anterior eye part is included in a preset region in this photograph image, wherein
the controller controls the first driver when the image of the anterior eye part is included in the preset region, and controls the second driver when the image of the anterior eye part is not included in the preset region.

21. The ophthalmologic apparatus of claim 1, wherein each of the two or more imaging parts comprises an optical system,
further comprising a second storage configured to previously store aberration information relating distortion aberration occurring in photograph images due to the optical system for each of the two or more imaging parts, wherein
the analyzer comprises a correction part configured to correct distortion of each of the two or more photograph images based on the aberration information, and obtains the three-dimensional position of the eye based on the two or more photograph images corrected.

22. The ophthalmologic apparatus of claim 21, wherein the aberration information is generated, for each of the two or more imaging parts, by analyzing multiple photograph images acquired by photographing reference points using a concerned imaging part while changing its position relative to the reference points.

23. The ophthalmologic apparatus of claim 1, further comprising:
a photography moving part configured to move at least one of the two or more imaging parts; and
a judging part configured to analyze a photograph image acquired by at least one of the two or more imaging parts to judge whether or not an image of the anterior eye part is included in a preset region in this photograph image, wherein
when the image of the anterior eye part is not included in the preset region, the controller controls the photography moving part to move at least one of the two or more imaging parts in a direction away from the supporting part and/or a direction away from the optical axis of the examination optical system, and
after at least one of the two or more imaging parts are moved, the judging part executes the judgment again.

24. The ophthalmologic apparatus of claim 1, further comprising a judging part configured to analyze a photograph image acquired by at least one of the two or more imaging parts to judge whether or not an image of the anterior eye part is included in a preset region in this photograph image, wherein
when the image of the anterior eye part is not included in the preset region, the controller controls an output part to output warning information.

25. The ophthalmologic apparatus of claim 1, further comprising an image synthesis part configured to form a synthetic image of the two or more photograph images.

26. The ophthalmologic apparatus of claim 25, wherein the controller displays the synthetic image on a display.

27. The ophthalmologic apparatus of claim 1, wherein the controller displays at least one of the two or more photograph images on a display.

28. The ophthalmologic apparatus of claim 1, wherein the two or more imaging parts comprises two cameras provided at different positions that are deviated from an optical path of the examination optical system.

29. The ophthalmologic apparatus of claim 1, wherein the two or more imaging parts are provided at lower positions than the optical axis of the examination optical system.

30. The ophthalmologic apparatus of claim 2, further comprising:
a moving-image acquiring optical system configured to acquire a moving image of the anterior eye part of the eye, wherein a part of its optical path is shared with the examination optical system;
a projecting optical system configured to project a target for executing position matching of the examination optical system with the eye onto the eye; and
an operation part, wherein the controller controls the projecting optical system to project the target onto the eye, controls the moving-image acquiring optical system to acquire a moving image of the anterior eye part onto which the target is being projected, controls a display to display the acquired moving image, obtains relative position information indicating a relative position between the eye and the examination optical system based on the three-dimensional position obtained by the analyzer, displays the obtained relative position information on the display, and controls the first driver to move the examination optical system in accordance with an operation carried out by using the operation part.

31. The ophthalmologic apparatus of claim 30, wherein the relative position information includes relative positions in an optical-axis direction of the examination optical system and horizontal and vertical directions that are perpendicular to the optical-axis direction.

32. The ophthalmologic apparatus of claim 31, wherein the controller indicates the relative position in the optical-axis direction with a preset display color.

33. The ophthalmologic apparatus of claim 30, further comprising a storage configured to store measurement information of characteristics of the eye acquired in advance, wherein
the controller obtains the relative position information based on the three-dimensional position and the measurement information.

34. The ophthalmologic apparatus of claim 1, further comprising filters configured to intercept light of wavelengths other than those of environmental illumination, wherein the filters are arranged at positions between the two or more imaging parts and the eye.

35. An ophthalmologic apparatus comprising:
an examination optical system configured to carry out an examination of an eye;
a driver configured to move the examination optical system three-dimensionally;
two or more imaging parts configured to substantially simultaneously photograph an anterior eye part of the eye from different directions;
an analyzer configured to obtain a three-dimensional position of the eye by analyzing two or more photograph images acquired by the two or more imaging parts substantially simultaneously; and
a controller configured to control the driver based on the three-dimensional position in order that a position of the examination optical system and the three-dimensional position of the eye match each other in two axis directions both perpendicular to an optical axis direction of the examination optical system, and a distance between the examination optical system and the eye becomes a predetermined working distance in the optical axis direction,
wherein the analyzer comprises:
a characteristic position specifying part configured to analyze the two or more photograph images to specify characteristic positions in the photograph images that correspond to a predetermined characteristic part of the anterior eye part; and
a three-dimensional position calculating part configured to calculate, as the three-dimensional position of the eye, a three-dimensional position of the characteristic part based on positions of the two or more imaging parts and the characteristic positions in the two or more photograph images.

\* \* \* \* \*